(12) United States Patent
Kovacevich et al.

(10) Patent No.: US 11,466,084 B2
(45) Date of Patent: Oct. 11, 2022

(54) ANTI-PD-1 ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Brian Kovacevich, Snohomish, WA (US); Dong Xia, Redmond, WA (US); Anne E. Jensen, Mill Creek, WA (US); Jonathan K. Fallen, Quincy, MA (US); Blair Renshaw, Renton, WA (US); Jeffrey B. Adamo, Seattle, WA (US); Phil Tan, Edmonds, WA (US); Zeren Gao, Redmond, WA (US); Yi Zhu, Chengdu (CN)

(73) Assignee: SYSTIMMUNE, INC., Redmond, WA (US)

( * ) Notice: Subject to any disclaimer, the term of this patent is extended or adjusted under 35 U.S.C. 154(b) by 0 days.

(21) Appl. No.: 16/615,113

(22) PCT Filed: Jun. 22, 2018

(86) PCT No.: PCT/US2018/039147
§ 371 (c)(1),
(2) Date: Nov. 19, 2019

(87) PCT Pub. No.: WO2019/005635
PCT Pub. Date: Jan. 3, 2019

(65) Prior Publication Data
US 2020/0157219 A1    May 21, 2020

Related U.S. Application Data

(60) Provisional application No. 62/545,603, filed on Aug. 15, 2017, provisional application No. 62/524,558, filed on Jun. 25, 2017, provisional application No. 62/524,554, filed on Jun. 25, 2017, provisional application No. 62/524,553, filed on Jun. 25, 2017, provisional application No. 62/524,557, filed on Jun. 25, 2017.

(51) Int. Cl.
*C07K 16/28*    (2006.01)

(52) U.S. Cl.
CPC ...... *C07K 16/2818* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,180,370 B1 * | 1/2001 | Queen | A61P 31/12 435/69.6 |
|---|---|---|---|
| 7,521,051 B2 * | 4/2009 | Collins | A61P 1/04 424/143.1 |
| 2016/0193334 A1 * | 7/2016 | Strack | C07K 16/2818 424/133.1 |

OTHER PUBLICATIONS

Lubert Stryer, Biochemistry, 4th, WH Freeman, New York (1995) ISBN: 0-7167-2009-4 (Year: 1995).*
Colman, Peter M. "Effects of amino acid sequence changes on antibody-antigen interactions." Research in Immunology 145.1 (1994): 33-36. (Year: 1994).*
Janeway, A. C., et al. "Immunobiology: the immune system in health and disease. London." Current Biology (1997): 3:1-3:11. (Year: 1997).*
Sela-Culang, Inbal, Vered Kunik, and Yanay Ofran. "The structural basis of antibody-antigen recognition." Frontiers in immunology 4 (2013): 302 (Year: 2013).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*

* cited by examiner

*Primary Examiner* — Michael Szperka
*Assistant Examiner* — Lia E Taylor
(74) *Attorney, Agent, or Firm* — Zhihua Han

(57) ABSTRACT

The application provides anti-PD-1 monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

16 Claims, 5 Drawing Sheets

Specification includes a Sequence Listing.

FIGURE 1

FIGURE 1 shows rabbit IgG antibodies in B cell culture supernatant binding to recombinant PD-1.

| plate 5. 0.75 PD-1+IgG+ cells/well | | | | | | | | | | | | |
|---|---|---|---|---|---|---|---|---|---|---|---|---|
|   | 1 | 2 | 3 | 4 | 5 | 6 | 7 | 8 | 9 | 10 | 11 | 12 |
| A | 0.241 | 0.33 | 0.224 | 0.216 | 0.125 | 0.13 | 0.146 | 0.124 | 0.135 | 0.101 | 0.13 | 0.127 |
| B | 0.145 | 0.225 | 0.172 | 0.178 | 0.2 | 0.171 | 0.198 | 0.386 | 0.139 | 0.086 | 0.148 | 0.173 |
| C | 0.18 | 0.161 | 0.165 | 0.168 | 0.173 | 0.168 | 0.134 | 0.181 | 0.112 | 0.107 | 0.15 | 0.134 |
| D | 0.125 | 0.185 | 0.132 | 2.139 | 0.126 | 0.143 | 0.121 | 0.204 | 0.142 | 0.134 | 0.14 | 0.126 |
| E | 0.121 | 0.194 | 0.178 | 0.209 | 0.186 | 0.25 | 0.181 | 0.163 | 0.202 | 0.131 | 0.147 | 0.157 |
| F | 0.154 | 0.145 | 0.119 | 0.142 | 0.136 | 0.19 | 0.188 | 0.145 | 0.137 | 2.722 | 0.158 | 0.129 |
| G | 0.157 | 0.144 | 0.087 | 0.146 | 0.151 | 0.137 | 0.253 | 0.152 | 0.143 | 0.164 | 0.138 | 0.146 |
| H | 0.144 | 0.171 | 0.123 | 0.164 | 0.137 | 0.097 | 0.146 | 0.143 | 0.129 | 0.132 | 0.157 | 0.201 |

FIGURE 2 FACS analysis of recombinant humanized PD-1 specific antibodies binding to PD-1 expressed on Jurkat cells.

FIGURE 3 FACS analysis of recombinant humanized PD-1 specific antibodies inhibiting binding of recombinant human PD-L1 binding to PD-1 expressed on Jurkat cells.

FIGURE 4 FACS analysis of recombinant humanized PD-1 specific antibodies inhibiting binding of recombinant human PD-L2 binding to PD-1 expressed on Jurkat cells.

FIGURE 5 show that PD-1 specific chimeric antibodies enhance non-antigen specific SEB induced T cell responses.

SEQUENCE LISTING

<160> NUMBER OF SEQ ID NOS: 80

<210> SEQ ID NO 1
<211> LENGTH: 654
<212> TYPE: DNA
<213> ORGANISM: Artificial Sequence
<220> FEATURE:
<223> OTHER INFORMATION: synthesized

<400> SEQUENCE: 1

```
caagtgctga cccagactgc atcgtccgtg tctgcagctg tgggaggcac agtcaccatc    60
agttgccagt ccagtcagag tgtttatgat aacaactggt tagcctggta tcagcagaaa   120
ccagggcagc ctcccatgct cctgatctat acagtatcca ctctggcatc tggggtctca   180
tcgcggttca aaggcagtgg atctgggaca cagttcactc tcaccatcag cggcgtgcag   240
tgtgacgatg ctgccactta ctactgtcaa ggcacttatt atagtagtgg ttggaacttt   300
gctttcggcg gagggaccga ggtggtggtc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc    600 acccatcagg gcctgagctc gcccgtcaca aagagcttca caggggaga gtgt           654
```

<210> SEQ ID NO 2
<211> LENGTH: 333
<212> TYPE: DNA
<213> ORGANISM: Artificial Sequence
<220> FEATURE:
<223> OTHER INFORMATION: synthesized

<400> SEQUENCE: 2

```
caagtgctga cccagactgc atcgtccgtg tctgcagctg tgggaggcac agtcaccatc    60
agttgccagt ccagtcagag tgtttatgat aacaactggt tagcctggta tcagcagaaa   120
```

```
ccagggcagc ctcccatgct cctgatctat acagtatcca ctctggcatc tggggtctca    180
tcgcggttca aaggcagtgg atctgggaca cagttcactc tcaccatcag cggcgtgcag    240
tgtgacgatg ctgccactta ctactgtcaa ggcacttatt atagtagtgg ttggaacttt    300
gctttcggcg agggaccga ggtggtggtc aaa                                   333
```

<210> SEQ ID NO 3
<211> LENGTH: 218
<212> TYPE: PRT
<213> ORGANISM: Artificial Sequence
<220> FEATURE:
<223> OTHER INFORMATION: synthesized

<400> SEQUENCE: 3

```
Gln Val Leu Thr Gln Thr Ala Ser Ser Val Ser Ala Ala Val Gly Gly
1               5                   10                  15

Thr Val Thr Ile Ser Cys Gln Ser Ser Gln Ser Val Tyr Asp Asn Asn
            20                  25                  30

Trp Leu Ala Trp Tyr Gln Gln Lys Pro Gly Gln Pro Pro Met Leu Leu
        35                  40                  45

Ile Tyr Thr Val Ser Thr Leu Ala Ser Gly Val Ser Ser Arg Phe Lys
50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Gln Gly Thr Tyr Tyr Ser Ser
                85                  90                  95

Gly Trp Asn Phe Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 4
<211> LENGTH: 111
<212> TYPE: PRT
<213> ORGANISM: Artificial Sequence
<220> FEATURE:
<223> OTHER INFORMATION: synthesized

<400> SEQUENCE: 4

```
Gln Val Leu Thr Gln Thr Ala Ser Ser Val Ser Ala Ala Val Gly Gly
1               5                   10                  15

Thr Val Thr Ile Ser Cys Gln Ser Ser Gln Ser Val Tyr Asp Asn Asn
            20                  25                  30

Trp Leu Ala Trp Tyr Gln Gln Lys Pro Gly Gln Pro Pro Met Leu Leu
        35                  40                  45
```

```
Ile Tyr Thr Val Ser Thr Leu Ala Ser Gly Val Ser Ser Arg Phe Lys
 50                  55                  60

Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Gln Gly Thr Tyr Tyr Ser Ser
                 85                  90                  95

Gly Trp Asn Phe Ala Phe Gly Gly Gly Thr Glu Val Val Val Lys
            100                 105                 110
```

<210> SEQ ID NO 5
<211> LENGTH: 1341
<212> TYPE: DNA
<213> ORGANISM: Artificial Sequence
<220> FEATURE:
<223> OTHER INFORMATION: synthesized

<400> SEQUENCE: 5

```
cagtcgttgg aggagtccgg gggagacctg gtcaagcctg agggatccct gacactcacc        60
tgcaaagcct ctggattcga cttcagtagc ggctactgga tatgctgggt ccgccaggct       120
ccagggaagg ggctggagtt gatcgcatgc atttatgctg gtactagtgg tagtacttcc       180
tacgcgagct gggcgagagg ccgattcacc atctccgaaa cctcgtcgac cacggtgact       240
ctgcaaatga ccagtctgac agccgcggac tcggccacct atttctgtgc gagaaatctt       300
tacacttaca atagccttgt gggccagggc accctggtca ccgtctcgag cgctagcacc       360
aagggcccat cggtcttccc cctggcaccc tcctccaaga gcacctctgg gggcacagcg       420
gccctgggct gcctggtcaa ggactacttc cccgaaccgg tgacggtgtc gtggaactca       480
ggcgccctga ccagcggcgt gcacaccttc ccggctgtcc tacagtcctc aggactctac       540
tccctcagca gcgtggtgac cgtgccctcc agcagcttgg gcacccagac ctacatctgc       600
aacgtgaatc acaagcccag caacaccaag gtggacaaga gagttgagcc caaatcttgt       660
gacaaaactc acacatgccc accgtgccca gcacctgaac tcctgggggg accgtcagtc       720
ttcctcttcc ccccaaaacc caaggacacc ctcatgatct cccggacccc tgaggtcaca       780
tgcgtggtgg tggacgtgag ccacgaagac cctgaggtca agttcaactg gtacgtggac       840
ggcgtggagg tgcataatgc caagacaaag ccgcgggagg agcagtacaa cagcacgtac       900
cgtgtggtca gcgtcctcac cgtcctgcac caggactggc tgaatggcaa ggagtacaag       960
tgcaaggtct ccaacaaagc cctcccagcc cccatcgaga aaaccatctc caaagccaaa      1020
gggcagcccc gagaaccaca ggtgtacacc ctgcccccat cccgggagga gatgaccaag      1080
aaccaggtca gcctgacctg cctggtcaaa ggcttctatc ccagcgacat cgccgtggag      1140
tgggagagca atgggcagcc ggagaacaac tacaagacca cgcctcccgt gctggactcc      1200
gacggctcct tcttcctcta tagcaagctc accgtggaca agagcaggtg gcagcagggg      1260
aacgtcttct catgctccgt gatgcatgag gctctgcaca accactacac gcagaagagc      1320
ctctccctgt ctccgggtaa a                                                1341
```

<210> SEQ ID NO 6
<211> LENGTH: 351
<212> TYPE: DNA
<213> ORGANISM: Artificial Sequence
<220> FEATURE:
<223> OTHER INFORMATION: synthesized

<400> SEQUENCE: 6

```
cagtcgttgg aggagtccgg gggagacctg gtcaagcctg agggatccct gacactcacc        60
```

```
tgcaaagcct ctggattcga cttcagtagc ggctactgga tatgctgggt ccgccaggct    120
ccagggaagg ggctggagtt gatcgcatgc atttatgctg gtactagtgg tagtacttcc    180
tacgcgagct gggcgagagg ccgattcacc atctccgaaa cctcgtcgac cacggtgact    240
ctgcaaatga ccagtctgac agccgcggac tcggccacct atttctgtgc gagaaatctt    300
tacacttaca atagcttgtg gggccagggc accctggtca ccgtctcgag c             351
```

<210> SEQ ID NO 7
<211> LENGTH: 447
<212> TYPE: PRT
<213> ORGANISM: Artificial Sequence
<220> FEATURE:
<223> OTHER INFORMATION: synthesized

<400> SEQUENCE: 7

```
Gln Ser Leu Glu Glu Ser Gly Gly Asp Leu Val Lys Pro Glu Gly Ser
1               5                   10                  15

Leu Thr Leu Thr Cys Lys Ala Ser Gly Phe Asp Phe Ser Ser Gly Tyr
            20                  25                  30

Trp Ile Cys Trp Val Arg Gln Ala Pro Gly Lys Gly Leu Glu Leu Ile
        35                  40                  45

Ala Cys Ile Tyr Ala Gly Thr Ser Gly Ser Thr Ser Tyr Ala Ser Trp
    50                  55                  60

Ala Arg Gly Arg Phe Thr Ile Ser Glu Thr Ser Ser Thr Thr Val Thr
65                  70                  75                  80

Leu Gln Met Thr Ser Leu Thr Ala Ala Asp Ser Ala Thr Tyr Phe Cys
                85                  90                  95

Ala Arg Asn Leu Tyr Thr Tyr Asn Ser Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
```

```
                305                 310                 315                 320
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
                435                 440                 445

<210> SEQ ID NO 8
<211> LENGTH: 117
<212> TYPE: PRT
<213> ORGANISM: Artificial Sequence
<220> FEATURE:
<223> OTHER INFORMATION: synthesized

<400> SEQUENCE: 8

Gln Ser Leu Glu Glu Ser Gly Gly Asp Leu Val Lys Pro Glu Gly Ser
1               5                   10                  15

Leu Thr Leu Thr Cys Lys Ala Ser Gly Phe Asp Phe Ser Ser Gly Tyr
                20                  25                  30

Trp Ile Cys Trp Val Arg Gln Ala Pro Gly Lys Gly Leu Glu Leu Ile
            35                  40                  45

Ala Cys Ile Tyr Ala Gly Thr Ser Gly Ser Thr Ser Tyr Ala Ser Trp
    50                  55                  60

Ala Arg Gly Arg Phe Thr Ile Ser Glu Thr Ser Ser Thr Thr Val Thr
65                  70                  75                  80

Leu Gln Met Thr Ser Leu Thr Ala Ala Asp Ser Ala Thr Tyr Phe Cys
                85                  90                  95

Ala Arg Asn Leu Tyr Thr Tyr Asn Ser Leu Trp Gly Gln Gly Thr Leu
                100                 105                 110

Val Thr Val Ser Ser
        115

<210> SEQ ID NO 9
<211> LENGTH: 657
<212> TYPE: DNA
<213> ORGANISM: Artificial Sequence
<220> FEATURE:
<223> OTHER INFORMATION: synthesized

<400> SEQUENCE: 9
gacatccaga tgacccagtc tccttccacc ctgtctgcat ctgtaggaga cagagtcacc      60
atcacttgcc agtccagtca gagtgtttat gataacaact ggttagcctg gtatcagcag    120
aaaccaggga agcccctaag ctcctgatct atacagtat ccactctggc atctggggtc    180
ccatcaaggt tcagcggcag tggatctggg acagaattca ctctcaccat cagcagcctg    240
cagcctgatg attttgcaac ttattactgc caaggcactt attatagtag tggttggaac    300
```

```
tttgctttcg gcggagggac caaggtggag atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt      657
```

<210> SEQ ID NO 10
<211> LENGTH: 336
<212> TYPE: DNA
<213> ORGANISM: Artificial Sequence
<220> FEATURE:
<223> OTHER INFORMATION: synthesized

<400> SEQUENCE: 10

```
gacatccaga tgacccagtc tccttccacc ctgtctgcat ctgtaggaga cagagtcacc    60
atcacttgcc agtccagtca gagtgtttat gataacaact ggttagcctg gtatcagcag   120
aaaccaggga agcccctaa gctcctgatc tatacagtat ccactctggc atctggggtc   180
ccatcaaggt tcagcggcag tggatctggg acagaattca ctctcaccat cagcagcctg   240
cagcctgatg attttgcaac ttattactgc caaggcactt attatagtag tggttggaac   300
tttgctttcg gcggagggac caaggtggag atcaaa                              336
```

<210> SEQ ID NO 11
<211> LENGTH: 219
<212> TYPE: PRT
<213> ORGANISM: Artificial Sequence
<220> FEATURE:
<223> OTHER INFORMATION: synthesized

<400> SEQUENCE: 11

```
Asp Ile Gln Met Thr Gln Ser Pro Ser Thr Leu Ser Ala Ser Val Gly
 1               5                  10                  15

Asp Arg Val Thr Ile Thr Cys Gln Ser Ser Gln Ser Val Tyr Asp Asn
            20                  25                  30

Asn Trp Leu Ala Trp Tyr Gln Gln Lys Pro Gly Lys Ala Pro Lys Leu
        35                  40                  45

Leu Ile Tyr Thr Val Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gly Thr Tyr Tyr Ser
                85                  90                  95

Ser Gly Trp Asn Phe Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
```

```
                180             185                 190
Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 12
<211> LENGTH: 112
<212> TYPE: PRT
<213> ORGANISM: Artificial Sequence
<220> FEATURE:
<223> OTHER INFORMATION: synthesized

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Asp Asn
            20                  25                  30

Asn Trp Leu Ala Trp Tyr Gln Gln Lys Pro Gly Lys Ala Pro Lys Leu
        35                  40                  45

Leu Ile Tyr Thr Val Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gly Tyr Tyr Tyr Ser
                85                  90                  95

Ser Gly Trp Asn Phe Ala Phe Gly Gly Gly Thr Lys Val Glu Ile Lys
            100                 105                 110

<210> SEQ ID NO 13
<211> LENGTH: 1341
<212> TYPE: DNA
<213> ORGANISM: Artificial Sequence
<220> FEATURE:
<223> OTHER INFORMATION: synthesized

<400> SEQUENCE: 13
gaggtgcagc tggtggagtc tgggggaggc ttggtccagc ctggggggtc cctgagactc      60
tcctgtgcag cctctggatt cgacttcagt agcggctact ggatatgctg ggtccgccag     120
gctccaggga aggggctgga gttgatcgca tgcatttatg ctggtactag tggtagtact     180
tcctacgcga gctgggcgag aggcagattc accatctccg aaacctccaa gaacacggtg     240
actcttcaaa tgaacagcct gagagccgag gactcggctg tgtattactg tgcgagaaat     300
ctttacactt acaatagctt gtggggccag ggaaccctgg tcaccgtctc gagcgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcacccca gacctacatc     600
tgcaacgtga atcacaagcc cagcaacacc aaggtggaca agagagttga gcccaaatct     660
tgtgacaaaa ctcacacatg cccaccgtgc ccagcacctg aagccgcggg ggcaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
```

```
taccgtgtgg tcagcgtcct caccgtcctg caccaggact ggctgaatgg caaggagtac    960
aagtgcgcgg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctatagcaag ctcaccgtgg acaagagcag gtggcagcag   1260
gggaacgtct tctcatgctc cgtgatgcat gaggctctgc acaaccacta cacgcagaag   1320
agcctctccc tgtctccggg t                                             1341

<210> SEQ ID NO 14
<211> LENGTH: 354
<212> TYPE: DNA
<213> ORGANISM: Artificial Sequence
<220> FEATURE:
<223> OTHER INFORMATION: synthesized

<400> SEQUENCE: 14
gaggtgcagc tggtggagtc tgggggaggc ttggtccagc ctgggggtc cctgagactc      60 tcctgtgcag cctctggatt cgacttcagt agcggctact ggatatgctg ggtccgccag    120
gctccaggga aggggctgga gttgatcgca tgcatttatg ctggtactag tggtagtact    180
tcctacgcga gctgggcgag aggcagattc accatctccg aaacctccaa gaacacggtg    240
actcttcaaa tgaacagcct gagagccgag gactcggctg tgtattactg tgcgagaaat    300
ctttacactt acaatagctt gtggggccag ggaaccctgg tcaccgtctc gagc          354

<210> SEQ ID NO 15
<211> LENGTH: 447
<212> TYPE: PRT
<213> ORGANISM: Artificial Sequence
<220> FEATURE:
<223> OTHER INFORMATION: synthesized

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser Gly
            20                  25                  30

Tyr Trp Ile Cys Trp Val Arg Gln Ala Pro Gly Lys Gly Leu Glu Leu
        35                  40                  45

Ile Ala Cys Ile Tyr Ala Gly Thr Ser Gly Ser Thr Ser Tyr Ala Ser
    50                  55                  60

Trp Ala Arg Gly Arg Phe Thr Ile Ser Glu Thr Ser Lys Asn Thr Val
65                  70                  75                  80

Thr Leu Gln Met Asn Ser Leu Arg Ala Glu Asp Ser Ala Val Tyr Tyr
                85                  90                  95

Cys Ala Arg Asn Leu Tyr Thr Tyr Asn Ser Leu Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                165                 170                 175
Ser Ser Gly Leu Tyr Ser Leu Ser Ser Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Ala Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 16
<211> LENGTH: 118
<212> TYPE: PRT
<213> ORGANISM: Artificial Sequence
<220> FEATURE:
<223> OTHER INFORMATION: synthesized

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Ser Gly
            20                  25                  30

Tyr Trp Ile Cys Trp Val Arg Gln Ala Pro Gly Lys Gly Leu Glu Leu
        35                  40                  45

Ile Ala Cys Ile Tyr Ala Gly Thr Ser Gly Ser Thr Ser Tyr Ala Ser
    50                  55                  60

Trp Ala Arg Gly Arg Phe Thr Ile Ser Glu Thr Ser Lys Asn Thr Val
65                  70                  75                  80

Thr Leu Gln Met Asn Ser Leu Arg Ala Glu Asp Ser Ala Val Tyr Tyr
```

85                  90                  95

Cys Ala Arg Asn Leu Tyr Thr Tyr Asn Ser Leu Trp Gly Gln Gly Thr
            100                 105                 110

Leu Val Thr Val Ser Ser
        115

<210> SEQ ID NO 17
<211> LENGTH: 651
<212> TYPE: DNA
<213> ORGANISM: Artificial Sequence
<220> FEATURE:
<223> OTHER INFORMATION: synthesized

<400> SEQUENCE: 17
gatgttgtga tgacccagac tccagcctcc gtgtctgcag ttgtgggagg cacagtcacc     60
atcaagtgcc aggccagtca gagcatttac agctacttaa actggtatca gcagaaacca    120
gggcagcctc ccaagctcct gatctatggt gcatccaatc tggcatctgg ggtctcatcg    180
cgattcaaag gcagtggatc tgggacagag ttcactctca ccatcagcga cctggagtgt    240
gccgatgctg ccacttacta ctgtcaatgt agttggttga gtggtgctgt tggtaatgct    300
ttcggcggag ggaccgaggt ggtggtcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t              651

<210> SEQ ID NO 18
<211> LENGTH: 330
<212> TYPE: DNA
<213> ORGANISM: Artificial Sequence
<220> FEATURE:
<223> OTHER INFORMATION: synthesized

<400> SEQUENCE: 18
gatgttgtga tgacccagac tccagcctcc gtgtctgcag ttgtgggagg cacagtcacc     60
atcaagtgcc aggccagtca gagcatttac agctacttaa actggtatca gcagaaacca    120
gggcagcctc ccaagctcct gatctatggt gcatccaatc tggcatctgg ggtctcatcg    180
cgattcaaag gcagtggatc tgggacagag ttcactctca ccatcagcga cctggagtgt    240
gccgatgctg ccacttacta ctgtcaatgt agttggttga gtggtgctgt tggtaatgct    300
ttcggcggag ggaccgaggt ggtggtcaaa                                     330

<210> SEQ ID NO 19
<211> LENGTH: 217
<212> TYPE: PRT
<213> ORGANISM: Artificial Sequence
<220> FEATURE:
<223> OTHER INFORMATION: synthesized

<400> SEQUENCE: 19

Asp Val Val Met Thr Gln Thr Pro Ala Ser Val Ser Ala Val Val Gly
1               5                   10                  15

Gly Thr Val Thr Ile Lys Cys Gln Ala Ser Gln Ser Ile Tyr Ser Tyr
            20                  25                  30

Leu Asn Trp Tyr Gln Gln Lys Pro Gly Gln Pro Pro Lys Leu Leu Ile

```
                35                  40                  45
Tyr Gly Ala Ser Asn Leu Ala Ser Gly Val Ser Ser Arg Phe Lys Gly
 50                  55                  60
Ser Gly Ser Gly Thr Glu Phe Thr Leu Thr Ile Ser Asp Leu Glu Cys
 65                  70                  75                  80
Ala Asp Ala Ala Thr Tyr Tyr Cys Gln Cys Ser Trp Leu Ser Gly Ala
                 85                  90                  95
Val Gly Asn Ala Phe Gly Gly Gly Thr Glu Val Val Val Lys Arg Thr
                100                 105                 110
Val Ala Ala Pro Ser Val Phe Ile Phe Pro Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 20
<211> LENGTH: 110
<212> TYPE: PRT
<213> ORGANISM: Artificial Sequence
<220> FEATURE:
<223> OTHER INFORMATION: synthesized

<400> SEQUENCE: 20

Asp Val Val Met Thr Gln Thr Pro Ala Ser Val Ser Ala Val Val Gly
 1               5                  10                  15
Gly Thr Val Thr Ile Lys Cys Gln Ala Ser Gln Ser Ile Tyr Ser Tyr
                20                  25                  30
Leu Asn Trp Tyr Gln Gln Lys Pro Gly Gln Pro Pro Lys Leu Leu Ile
             35                  40                  45
Tyr Gly Ala Ser Asn Leu Ala Ser Gly Val Ser Ser Arg Phe Lys Gly
 50                  55                  60
Ser Gly Ser Gly Thr Glu Phe Thr Leu Thr Ile Ser Asp Leu Glu Cys
 65                  70                  75                  80
Ala Asp Ala Ala Thr Tyr Tyr Cys Gln Cys Ser Trp Leu Ser Gly Ala
                 85                  90                  95
Val Gly Asn Ala Phe Gly Gly Gly Thr Glu Val Val Val Lys
                100                 105                 110

<210> SEQ ID NO 21
<211> LENGTH: 1251
<212> TYPE: DNA
<213> ORGANISM: Artificial Sequence
<220> FEATURE:
<223> OTHER INFORMATION: synthesized

<400> SEQUENCE: 21
ggattctcct tcagtagcta ctggatgtgc tgggtccgcc aggctccagg gaaggggctg      60
gagtggatcg gatgcattac gactggtagt ggtagcactt actacgcgag ctgggcgaag     120
```

```
cgccgattca ccatctccaa aacctcgtcg accacggtga ctctgcaaat gaccagtctg      180
acagccgcgg acacgccac ctatttctgt acgagagcat ttgacttgtg gggcccgggg       240
accctggtca ccgtctcgag cgctagcacc aagggcccat cggtcttccc cctggcaccc      300
tcctccaaga gcacctctgg gggcacagcg gccctgggct gcctggtcaa ggactacttc      360
cccgaaccgg tgacggtgtc gtggaactca ggcgccctga ccagcggcgt gcacaccttc      420
ccggctgtcc tacagtcctc aggactctac tccctcagca gcgtggtgac cgtgccctcc      480
agcagcttgg gcacccagac ctacatctgc aacgtgaatc acaagcccag caacaccaag      540
gtggacaaga gagttgagcc caaatcttgt gacaaaactc acacatgccc accgtgccca      600
gcacctgaac tcctgggggg accgtcagtc ttcctcttcc ccccaaaacc caaggacacc      660
ctcatgatct cccggacccc tgaggtcaca tgcgtggtgg tggacgtgag ccacgaagac      720
cctgaggtca agttcaactg gtacgtggac ggcgtggagg tgcataatgc caagacaaag      780
ccgcgggagg agcagtacaa cagcacgtac cgtgtggtca gcgtcctcac cgtcctgcac      840
caggactggc tgaatggcaa ggagtacaag tgcaaggtct ccaacaaagc cctcccagcc      900
cccatcgaga aaaccatctc caaagccaaa gggcagcccc gagaaccaca ggtgtacacc      960
ctgcccccat cccgggagga gatgaccaag aaccaggtca gcctgacctg cctggtcaaa      1020
ggcttctatc ccagcgacat cgccgtggag tgggagagca atgggcagcc ggagaacaac      1080
tacaagacca cgcctcccgt gctggactcc gacggctcct tcttcctcta tagcaagctc      1140
accgtggaca agagcaggtg gcagcagggg aacgtcttct catgctccgt gatgcatgag      1200
gctctgcaca accactacac gcagaagagc ctctccctgt ctccgggtaa a              1251

<210> SEQ ID NO 22
<211> LENGTH: 336
<212> TYPE: DNA
<213> ORGANISM: Artificial Sequence
<220> FEATURE:
<223> OTHER INFORMATION: synthesized

<400> SEQUENCE: 22
caggagcaac tggtggagtc cggggggaggc ctggtccagc ctgagggatc cctgacactc       60
acctgcacag cttctggatt ctccttcagt agctactgga tgtgctgggt ccgccaggct      120
ccagggaagg ggctggagtg gatcggatgc attacgactg gtagtggtag cacttactac      180
gcgagctggg cgaagcgccg attcaccatc tccaaaacct cgtcgaccac ggtgactctg      240
caaatgacca gtctgacagc cgcggacacg gccacctatt tctgtacgag agcatttgac      300
ttgtggggcc cggggaccct ggtcaccgtc tcgagc                                 336

<210> SEQ ID NO 23
<211> LENGTH: 442
<212> TYPE: PRT
<213> ORGANISM: Artificial Sequence
<220> FEATURE:
<223> OTHER INFORMATION: synthesized

<400> SEQUENCE: 23

Gln Glu Gln Leu Val Glu Ser Gly Gly Gly Leu Val Gln Pro Glu Gly
 1               5                  10                  15

Ser Leu Thr Leu Thr Cys Thr Ala Ser Gly Phe Ser Phe Ser Ser Tyr
            20                  25                  30

Trp Met Cys Trp Val Arg Gln Ala Pro Gly Lys Gly Leu Glu Trp Ile
        35                  40                  45
```

Gly Cys Ile Thr Thr Gly Ser Gly Ser Thr Tyr Tyr Ala Ser Trp Ala
    50                  55                  60

Lys Arg Arg Phe Thr Ile Ser Lys Thr Ser Ser Thr Val Thr Leu
65                  70                  75                  80

Gln Met Thr Ser Leu Thr Ala Ala Asp Thr Ala Thr Tyr Phe Cys Thr
                85                  90                  95

Arg Ala Phe Asp Leu Trp Gly Pro Gly Thr Leu Val Thr Val Ser Ser
            100                 105                 110

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 24
<211> LENGTH: 112

<212> TYPE: PRT
<213> ORGANISM: Artificial Sequence
<220> FEATURE:
<223> OTHER INFORMATION: synthesized

<400> SEQUENCE: 24

```
Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Tyr
            20                  25                  30

Trp Met Cys Trp Val Arg Gln Ala Pro Gly Lys Gly Leu Glu Trp Ile
        35                  40                  45

Gly Cys Ile Thr Thr Gly Ser Gly Ser Thr Tyr Tyr Ala Ser Trp Ala
    50                  55                  60

Lys Arg Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Thr
                85                  90                  95

Arg Ala Phe Asp Leu Trp Gly Pro Gly Thr Leu Val Thr Val Ser Ser
            100                 105                 110
```

<210> SEQ ID NO 25
<211> LENGTH: 651
<212> TYPE: DNA
<213> ORGANISM: Artificial Sequence
<220> FEATURE:
<223> OTHER INFORMATION: synthesized

<400> SEQUENCE: 25

```
gacatccaga tgacccagtc tccatcctcc ctgtctgcat ctgtaggaga cagagtcacc      60
atcacttgcc aggccagtca gagcatttac agctacttaa ctggtatca gcagaaacca     120
gggaaagccc ctaagctcct gatctatggt gcatccaatc tggcatctgg ggtcccatca    180
aggttcagtg gcagtggatc tgggacagat ttcactctca ccatcagcag tctgcaacct    240
gaagattttg caacttacta ctgtcaaagc agttggttga gtggtgctgt tggtaatgct    300
ttcggcggag ggaccaaggt ggagatcaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t              651
```

<210> SEQ ID NO 26
<211> LENGTH: 330
<212> TYPE: DNA
<213> ORGANISM: Artificial Sequence
<220> FEATURE:
<223> OTHER INFORMATION: synthesized

<400> SEQUENCE: 26

```
gacatccaga tgacccagtc tccatcctcc ctgtctgcat ctgtaggaga cagagtcacc      60
atcacttgcc aggccagtca gagcatttac agctacttaa ctggtatca gcagaaacca     120
gggaaagccc ctaagctcct gatctatggt gcatccaatc tggcatctgg ggtcccatca    180
aggttcagtg gcagtggatc tgggacagat ttcactctca ccatcagcag tctgcaacct    240
gaagattttg caacttacta ctgtcaaagc agttggttga gtggtgctgt tggtaatgct    300
```

```
ttcggcggag ggaccaaggt ggagatcaaa                                     330
```

<210> SEQ ID NO 27
<211> LENGTH: 217
<212> TYPE: PRT
<213> ORGANISM: Artificial Sequence
<220> FEATURE:
<223> OTHER INFORMATION: synthesized

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Trp Leu Ser Gly Ala
                85                  90                  95

Val Gly Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 28
<211> LENGTH: 110
<212> TYPE: PRT
<213> ORGANISM: Artificial Sequence
<220> FEATURE:
<223> OTHER INFORMATION: synthesized

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Tyr Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Ser Ser Trp Leu Ser Gly Ala
                85                  90                  95

Val Gly Asn Ala Phe Gly Gly Gly Thr Lys Val Glu Ile Lys
        100                 105                 110

<210> SEQ ID NO 29
<211> LENGTH: 1326
<212> TYPE: DNA
<213> ORGANISM: Artificial Sequence
<220> FEATURE:
<223> OTHER INFORMATION: synthesized

<400> SEQUENCE: 29

| | | | | |
|---|---|---|---|---|
| caggagcagc | tgttggagtc | tgggggaggc | ttggtacagc | ctgggggtc cctgagactc | 60 |
| tcctgtacag | cctctggatt | ctcctttagc | agctactgga | tgtgctgggt ccgccaggct | 120 |
| ccagggaagg | ggctggagtg | gatcggatgc | attacgactg | gtagtggtag cacttactac | 180 |
| gcgagctggg | cgaagcgccg | gttcaccatc | tccaaagaca | attccaagaa cacggtgact | 240 |
| ctgcaaatga | acagcctgag | agccgaggac | acggccgtat | attactgtac gagagcattt | 300 |
| gacttgtggg | gccagggaac | cctggtcacc | gtctcgagcg | ctagcaccaa gggcccatcg | 360 |
| gtcttccccc | tggcaccctc | ctccaagagc | acctctgggg | gcacagcggc cctgggctgc | 420 |
| ctggtcaagg | actacttccc | cgaaccggtg | acggtgtcgt | ggaactcagg cgccctgacc | 480 |
| agcggcgtgc | acaccttccc | ggctgtccta | cagtcctcag | gactctactc cctcagcagc | 540 |
| gtggtgaccg | tgccctccag | cagcttgggc | acccagacct | acatctgcaa cgtgaatcac | 600 |
| aagcccagca | acaccaaggt | ggacaagaga | gttgagccca | aatcttgtga caaaactcac | 660 |
| acatgcccac | cgtgcccagc | acctgaagcc | gcggggggcac | cgtcagtctt cctcttcccc | 720 |
| ccaaaaccca | aggacaccct | catgatctcc | cggacccctg | aggtcacatg cgtggtggtg | 780 |
| gacgtgagcc | acgaagaccc | tgaggtcaag | ttcaactggt | acgtggacgg cgtggaggtg | 840 |
| cataatgcca | agacaaagcc | gcgggaggag | cagtacaaca | gcacgtaccg tgtggtcagc | 900 |
| gtcctcaccg | tcctgcacca | ggactggctg | aatggcaagg | agtacaagtg cgcggtctcc | 960 |
| aacaaagccc | tcccagcccc | catcgagaaa | accatctcca | aagccaaagg gcagccccga | 1020 |
| gaaccacagg | tgtacaccct | gcccccatcc | cgggatgagc | tgaccaagaa ccaggtcagc | 1080 |
| ctgacctgcc | tggtcaaagg | cttctatccc | agcgacatcg | ccgtggagtg ggagagcaat | 1140 |
| gggcagccgg | agaacaacta | caagaccacg | cctcccgtgc | tggactccga cggctccttc | 1200 |
| ttcctctata | gcaagctcac | cgtggacaag | agcaggtggc | agcaggggaa cgtcttctca | 1260 |
| tgctccgtga | tgcatgaggc | tctgcacaac | cactacacgc | agaagagcct ctccctgtct | 1320 |
| ccgggt | | | | | 1326 |

<210> SEQ ID NO 30
<211> LENGTH: 339
<212> TYPE: DNA
<213> ORGANISM: Artificial Sequence
<220> FEATURE:
<223> OTHER INFORMATION: synthesized

<400> SEQUENCE: 30

| | | | | |
|---|---|---|---|---|
| caggagcagc | tgttggagtc | tgggggaggc | ttggtacagc | ctgggggtc cctgagactc | 60 |
| tcctgtacag | cctctggatt | ctcctttagc | agctactgga | tgtgctgggt ccgccaggct | 120 |
| ccagggaagg | ggctggagtg | gatcggatgc | attacgactg | gtagtggtag cacttactac | 180 |

```
gcgagctggg cgaagcgccg gttcaccatc tccaaagaca attccaagaa cacggtgact    240
ctgcaaatga acagcctgag agccgaggac acggccgtat attactgtac gagagcattt    300
gacttgtggg gccagggaac cctggtcacc gtctcgagc                           339
```

<210> SEQ ID NO 31
<211> LENGTH: 442
<212> TYPE: PRT
<213> ORGANISM: Artificial Sequence
<220> FEATURE:
<223> OTHER INFORMATION: synthesized

<400> SEQUENCE: 31

```
Gln Glu Gln Leu Leu Glu Ser Gly Gly Gly Leu Val Gln Pro Gly Gly
1               5                   10                  15

Ser Leu Arg Leu Ser Cys Thr Ala Ser Gly Phe Ser Phe Ser Ser Tyr
            20                  25                  30

Trp Met Cys Trp Val Arg Gln Ala Pro Gly Lys Gly Leu Glu Trp Ile
        35                  40                  45

Gly Cys Ile Thr Thr Gly Ser Gly Ser Thr Tyr Tyr Ala Ser Trp Ala
    50                  55                  60

Lys Arg Arg Phe Thr Ile Ser Lys Asp Asn Ser Lys Asn Thr Val Thr
65                  70                  75                  80

Leu Gln Met Asn Ser Leu Arg Ala Glu Asp Thr Ala Val Tyr Tyr Cys
                85                  90                  95

Thr Arg Ala Phe Asp Leu Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Ala Ala Gly Ala Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Ala Val Ser
305                 310                 315                 320

Asn Lys Ala Leu Pro Ala Pro Ile Glu Lys Thr Ile Ser Lys Ala Lys
                325                 330                 335
```

Gly Gln Pro Arg Glu Pro Gln Val Tyr Thr Leu Pro Pro Ser Arg Asp
                340                 345                 350

Glu Leu Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 32
<211> LENGTH: 113
<212> TYPE: PRT
<213> ORGANISM: Artificial Sequence
<220> FEATURE:
<223> OTHER INFORMATION: synthesized

<400> SEQUENCE: 32

Gln Glu Gln Leu Leu Glu Ser Gly Gly Gly Leu Val Gln Pro Gly Gly
1               5                   10                  15

Ser Leu Arg Leu Ser Cys Thr Ala Ser Gly Phe Ser Phe Ser Ser Tyr
            20                  25                  30

Trp Met Cys Trp Val Arg Gln Ala Pro Gly Lys Gly Leu Glu Trp Ile
        35                  40                  45

Gly Cys Ile Thr Thr Gly Ser Gly Ser Thr Tyr Tyr Ala Ser Trp Ala
    50                  55                  60

Lys Arg Arg Phe Thr Ile Ser Lys Asp Asn Ser Lys Asn Thr Val Thr
65                  70                  75                  80

Leu Gln Met Asn Ser Leu Arg Ala Glu Asp Thr Ala Val Tyr Tyr Cys
                85                  90                  95

Thr Arg Ala Phe Asp Leu Trp Gly Gln Gly Thr Leu Val Thr Val Ser
            100                 105                 110

Ser

<210> SEQ ID NO 33
<211> LENGTH: 645
<212> TYPE: DNA
<213> ORGANISM: Artificial Sequence
<220> FEATURE:
<223> OTHER INFORMATION: synthesized

<400> SEQUENCE: 33
caagtgctga cccagactcc atctcccgtg tctgcagctg tgggaggcac agtcagcatc      60
agttgccagt ccagtccgag tgtttatagt aactactttat cctggtttca gcagaaacca    120
gggcagcctc ccaagctcct gatctattat gcatccactc tggcatctgg ggtcccttcg    180
cggttcaaag gcagtggatc tgggacacag ttcactctca ccatcagcga cgtgcagtgt    240
gacgatgctg ccacttacta ctgtgcaggc ggttatagta gtagtactcg tgctttcggc    300
ggagggaccg aggtggtggt caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480

```
caggagagtg tcacagagca ggacagcaag gacagcacct acagcctcag cagcaccctg      540
acgctgagca aagcagacta cgagaaacac aaagtctacg cctgcgaagt cacccatcag      600
ggcctgagct cgcccgtcac aaagagcttc aacaggggag agtgt                     645
```

```
<210> SEQ ID NO 34
<211> LENGTH: 324
<212> TYPE: DNA
<213> ORGANISM: Artificial Sequence
<220> FEATURE:
<223> OTHER INFORMATION: synthesized

<400> SEQUENCE: 34
```

```
caagtgctga cccagactcc atctcccgtg tctgcagctg tgggaggcac agtcagcatc       60
agttgccagt ccagtccgag tgtttatagt aactacttat cctggtttca gcagaaacca      120
gggcagcctc ccaagctcct gatctattat gcatccactc tggcatctgg ggtcccttcg      180
cggttcaaag gcagtggatc tgggacacag ttcactctca ccatcagcga cgtgcagtgt      240
gacgatgctg ccacttacta ctgtgcaggc ggttatagta gtagtactcg tgctttcggc      300
ggagggaccg aggtggtggt caaa                                             324
```

```
<210> SEQ ID NO 35
<211> LENGTH: 215
<212> TYPE: PRT
<213> ORGANISM: Artificial Sequence
<220> FEATURE:
<223> OTHER INFORMATION: synthesized

<400> SEQUENCE: 35
```

Gln Val Leu Thr Gln Thr Pro Ser Pro Val Ser Ala Ala Val Gly Gly
1               5                   10                  15

Thr Val Ser Ile Ser Cys Gln Ser Ser Pro Ser Val Tyr Ser Asn Tyr
            20                  25                  30

Leu Ser Trp Phe Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Thr
                85                  90                  95

Arg Ala Phe Gly Gly Gly Thr Glu Val Val Val Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys

<210> SEQ ID NO 36
<211> LENGTH: 108
<212> TYPE: PRT
<213> ORGANISM: Artificial Sequence
<220> FEATURE:
<223> OTHER INFORMATION: synthesized

<400> SEQUENCE: 36

```
Gln Val Leu Thr Gln Thr Pro Ser Pro Val Ser Ala Ala Val Gly Gly
1               5                   10                  15

Thr Val Ser Ile Ser Cys Gln Ser Ser Pro Ser Val Tyr Ser Asn Tyr
            20                  25                  30

Leu Ser Trp Phe Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Ala Gly Gly Tyr Ser Ser Ser Thr
                85                  90                  95

Arg Ala Phe Gly Gly Gly Thr Glu Val Val Val Lys
            100                 105
```

<210> SEQ ID NO 37
<211> LENGTH: 1329
<212> TYPE: DNA
<213> ORGANISM: Artificial Sequence
<220> FEATURE:
<223> OTHER INFORMATION: synthesized

<400> SEQUENCE: 37

| | |
|---|---:|
| caggagcagg tgaaggagac cggggggaggc ctggtccagc ctgggggatc cctgacactc | 60 |
| tcctgcaaag cctctggatt taccatcagt agctatggag tgagctgggt ccgccaggct | 120 |
| ccagggaagg ggctggagtg gatcgcattg attttcctg gtattggttt caaagactac | 180 |
| gcgagctggg tgaatggccg attcaccctc tccagcgaca cgcccagaa cactgtggaa | 240 |
| cttcagatga acagtctgac agcggcggac acggccgcct atttctgtgc gagagatttg | 300 |
| gacttgtggg gccaagggac cctcgtcacc gtctcgagcg ctagcaccaa gggcccatcg | 360 |
| gtcttccccc tggcaccctc ctccaagagc acctctgggg gcacagcggc cctgggctgc | 420 |
| ctggtcaagg actacttccc cgaaccggtg acggtgtcgt ggaactcagg cgccctgacc | 480 |
| agcggcgtgc acaccttccc ggctgtccta cagtcctcag gactctactc cctcagcagc | 540 |
| gtggtgaccg tgccctccag cagcttgggc acccagacct acatctgcaa cgtgaatcac | 600 |
| aagcccagca acaccaaggt ggacaagaga gttgagccca atcttgtga caaaactcac | 660 |
| acatgcccac cgtgcccagc acctgaactc ctgggggac cgtcagtctt cctcttcccc | 720 |
| ccaaaaccca aggacaccct catgatctcc cggacccctg aggtcacatg cgtggtggtg | 780 |
| gacgtgagcc acgaagaccc tgaggtcaag ttcaactggt acgtggacgg cgtggaggtg | 840 |
| cataatgcca agacaaagcc gcgggaggag cagtacaaca gcacgtaccg tgtggtcagc | 900 |
| gtcctcaccg tcctgcacca ggactggctg aatggcaagg agtacaagtg caaggtctcc | 960 |
| aacaaagccc tcccagcccc catcgagaaa accatctcca aagccaaagg gcagccccga | 1020 |
| gaaccacagg tgtacaccct gcccccatcc cgggaggaga tgaccaagaa ccaggtcagc | 1080 |

```
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                            1329
```

<210> SEQ ID NO 38
<211> LENGTH: 339
<212> TYPE: DNA
<213> ORGANISM: Artificial Sequence
<220> FEATURE:
<223> OTHER INFORMATION: synthesized

<400> SEQUENCE: 38

```
caggagcagg tgaaggagac cggggggaggc ctggtccagc ctgggggatc cctgacactc     60
tcctgcaaag cctctggatt taccatcagt agctatggag tgagctgggt ccgccaggct    120
ccagggaagg ggctggagtg gatcgcattg attttcctg gtattggttt caaagactac    180
gcgagctggg tgaatggccg attcacccte tccagcgaca acgcccagaa cactgtggaa    240
cttcagatga acagtctgac agcggcggac acggccgcct atttctgtgc gagagatttg    300
gacttgtggg gccaagggac cctcgtcacc gtctcgagc                           339
```

<210> SEQ ID NO 39
<211> LENGTH: 443
<212> TYPE: PRT
<213> ORGANISM: Artificial Sequence
<220> FEATURE:
<223> OTHER INFORMATION: synthesized

<400> SEQUENCE: 39

```
Gln Glu Gln Val Lys Glu Thr Gly Gly Gly Leu Val Gln Pro Gly Gly
1               5                   10                  15

Ser Leu Thr Leu Ser Cys Lys Ala Ser Gly Phe Thr Ile Ser Ser Tyr
            20                  25                  30

Gly Val Ser Trp Val Arg Gln Ala Pro Gly Lys Gly Leu Glu Trp Ile
        35                  40                  45

Ala Leu Ile Phe Pro Gly Ile Gly Phe Lys Asp Tyr Ala Ser Trp Val
    50                  55                  60

Asn Gly Arg Phe Thr Leu Ser Ser Asp Asn Ala Gln Asn Thr Val Glu
65                  70                  75                  80

Leu Gln Met Asn Ser Leu Thr Ala Ala Asp Thr Ala Ala Tyr Phe Cys
                85                  90                  95

Ala Arg Asp Leu Asp Leu Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
```

-continued

```
                195                 200                 205
Lys Arg Val Glu Pro Lys Ser Cys Asp Lys Thr His Thr Cys Pro Pro
            210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
            275                 280                 285
Glu Glu Gln Tyr Asn Ser Thr Tyr Arg Val Val Ser Val Leu Thr Val
        290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
            435                 440

<210> SEQ ID NO 40
<211> LENGTH: 113
<212> TYPE: PRT
<213> ORGANISM: Artificial Sequence
<220> FEATURE:
<223> OTHER INFORMATION: synthesized

<400> SEQUENCE: 40

Gln Glu Gln Val Lys Glu Thr Gly Gly Gly Leu Val Gln Pro Gly Gly
1               5                   10                  15
Ser Leu Thr Leu Ser Cys Lys Ala Ser Gly Phe Thr Ile Ser Ser Tyr
            20                  25                  30
Gly Val Ser Trp Val Arg Gln Ala Pro Gly Lys Gly Leu Glu Trp Ile
        35                  40                  45
Ala Leu Ile Phe Pro Gly Ile Gly Phe Lys Asp Tyr Ala Ser Trp Val
    50                  55                  60
Asn Gly Arg Phe Thr Leu Ser Ser Asp Asn Ala Gln Asn Thr Val Glu
65                  70                  75                  80
Leu Gln Met Asn Ser Leu Thr Ala Asp Thr Ala Ala Tyr Phe Cys
                85                  90                  95
Ala Arg Asp Leu Asp Leu Trp Gly Gln Gly Thr Leu Val Thr Val Ser
            100                 105                 110
Ser
```

<210> SEQ ID NO 41
<211> LENGTH: 648
<212> TYPE: DNA
<213> ORGANISM: Artificial Sequence
<220> FEATURE:
<223> OTHER INFORMATION: synthesized

<400> SEQUENCE: 41

```
gacatccaga tgacccagtc tccatcctcc ctgtctgcat ctgtaggaga cagagtcacc      60
atcacttgcc agtccagtcc gagtgtttat agtaactact tatcctggta tcagcagaaa     120
ccagggaaag ttcctaagct cctgatctat tatgcatcca ctctggcatc tggggtccca     180
tctcggttca gtggcagtgg atctgggaca gatttcactc tcaccatcag cagcctgcag     240
cctgaagatg ttgcaactta ttactgtgca ggcggttata gtagtagtac tcgtgctttc     300
ggcggaggga ccaaggtgga gatcaaacgt acggtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgccctcca atcgggtaac     480
tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
cagggcctga gctcgcccgt cacaaagagc ttcaacaggg gagagtgt                   648
```

<210> SEQ ID NO 42
<211> LENGTH: 327
<212> TYPE: DNA
<213> ORGANISM: Artificial Sequence
<220> FEATURE:
<223> OTHER INFORMATION: synthesized

<400> SEQUENCE: 42

```
gacatccaga tgacccagtc tccatcctcc ctgtctgcat ctgtaggaga cagagtcacc      60
atcacttgcc agtccagtcc gagtgtttat agtaactact tatcctggta tcagcagaaa     120
ccagggaaag ttcctaagct cctgatctat tatgcatcca ctctggcatc tggggtccca     180
tctcggttca gtggcagtgg atctgggaca gatttcactc tcaccatcag cagcctgcag     240
cctgaagatg ttgcaactta ttactgtgca ggcggttata gtagtagtac tcgtgctttc     300
ggcggaggga ccaaggtgga gatcaaa                                         327
```

<210> SEQ ID NO 43
<211> LENGTH: 216
<212> TYPE: PRT
<213> ORGANISM: Artificial Sequence
<220> FEATURE:
<223> OTHER INFORMATION: synthesized

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Gln Ser Ser Pro Ser Val Tyr Ser Asn
            20                  25                  30

Tyr Leu Ser Trp Tyr Gln Gln Lys Pro Gly Lys Val Pro Lys Leu Leu
        35                  40                  45

Ile Tyr Tyr Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Ala Gly Gly Tyr Ser Ser Ser
                85                  90                  95

Thr Arg Ala Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 44
<211> LENGTH: 109
<212> TYPE: PRT
<213> ORGANISM: Artificial Sequence
<220> FEATURE:
<223> OTHER INFORMATION: synthesized

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Gln Ser Ser Pro Ser Val Tyr Ser Asn
            20                  25                  30

Tyr Leu Ser Trp Tyr Gln Gln Lys Pro Gly Lys Val Pro Lys Leu Leu
        35                  40                  45

Ile Tyr Tyr Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Ala Gly Gly Tyr Ser Ser Ser
                85                  90                  95

Thr Arg Ala Phe Gly Gly Gly Thr Lys Val Glu Ile Lys
            100                 105

<210> SEQ ID NO 45
<211> LENGTH: 1329
<212> TYPE: DNA
<213> ORGANISM: Artificial Sequence
<220> FEATURE:
<223> OTHER INFORMATION: synthesized

<400> SEQUENCE: 45
caggagcagg tgaaggagac cggggggaggc ttggtacagc ctggggggtc cctgagactc     60
tcctgtgcag cctctggatt caccatcagc agctatggag tgagctgggt ccgccaggct    120
ccagggaagg ggctggagtg ggtcgcattg atttttcccg ggattggttt caaagactac    180
gcgagctggg tgaatggccg gttcacccte tccagcgaca acgccagaa cactgtggaa    240 ctgcaaatga acagcctgag agccgaggac acggccgtat attactgtgc gagagatttg    300

```
gacttgtggg gccagggaac cctggtcacc gtctcgagcg ctagcaccaa gggcccatcg    360
gtcttccccc tggcaccctc ctccaagagc acctctgggg gcacagcggc cctgggctgc    420
ctggtcaagg actacttccc cgaaccggtg acggtgtcgt ggaactcagg cgccctgacc    480
agcggcgtgc acaccttccc ggctgtccta cagtcctcag gactctactc cctcagcagc    540
gtggtgaccg tgccctccag cagcttgggc acccagacct acatctgcaa cgtgaatcac    600
aagcccagca acaccaaggt ggacaagaga gttgagccca aatcttgtga caaaactcac    660
acatgcccac cgtgcccagc acctgaactc ctggggggac cgtcagtctt cctcttcccc    720
ccaaaaccca aggacaccct catgatctcc cggacccctg aggtcacatg cgtggtggtg    780
gacgtgagcc acgaagaccc tgaggtcaag ttcaactggt acgtggacgg cgtggaggtg    840
cataatgcca agacaaagcc gcgggaggag cagtacaaca gcacgtaccg tgtggtcagc    900
gtcctcaccg tcctgcacca ggactggctg aatggcaagg agtacaagtg caaggtctcc    960
aacaaagccc tcccagcccc catcgagaaa accatctcca agccaaaggg cagccccga     1020 gaaccacagg tgtacaccct gcccccatcc cgggaggaga tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctata gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                           1329

<210> SEQ ID NO 46
<211> LENGTH: 339
<212> TYPE: DNA
<213> ORGANISM: Artificial Sequence
<220> FEATURE:
<223> OTHER INFORMATION: synthesized

<400> SEQUENCE: 46
caggagcagg tgaaggagac cggggggaggc ttggtacagc ctggggggtc cctgagactc    60
tcctgtgcag cctctggatt caccatcagc agctatggag tgagctgggt ccgccaggct    120
ccagggaagg ggctggagtg ggtcgcattg atttttcccg ggattggttt caaagactac    180
gcgagctggg tgaatggccg gttcacccte tccagcgaca cgcccagaa cactgtggaa    240 ctgcaaatga acagcctgag agccgaggac acggccgtat attactgtgc gagagatttg    300
gacttgtggg gccagggaac cctggtcacc gtctcgagc                           339

<210> SEQ ID NO 47
<211> LENGTH: 443
<212> TYPE: PRT
<213> ORGANISM: Artificial Sequence
<220> FEATURE:
<223> OTHER INFORMATION: synthesized

<400> SEQUENCE: 47

Gln Glu Gln Val Lys Glu Thr Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Gly Val Ser Trp Val Arg Gln Ala Pro Gly Lys Gly Leu Glu Trp Val
        35                  40                  45

Ala Leu Ile Phe Pro Gly Ile Gly Phe Lys Asp Tyr Ala Ser Trp Val
    50                  55                  60
```

```
Asn Gly Arg Phe Thr Leu Ser Ser Asp Asn Ala Gln Asn Thr Val Glu
 65                  70                  75                  80

Leu Gln Met Asn Ser Leu Arg Ala Glu Asp Thr Ala Val Tyr Tyr Cys
                 85                  90                  95

Ala Arg Asp Leu Asp Leu Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 48
<211> LENGTH: 113
<212> TYPE: PRT
<213> ORGANISM: Artificial Sequence
<220> FEATURE:
```

<223> OTHER INFORMATION: synthesized

<400> SEQUENCE: 48

| Gln | Glu | Gln | Val | Lys | Glu | Thr | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Ile | Ser | Ser | Tyr |
|     |     | 20  |     |     |     |     | 25  |     |     |     |     | 30  |     |     |     |

| Gly | Val | Ser | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |

| Ala | Leu | Ile | Phe | Pro | Gly | Ile | Gly | Phe | Lys | Asp | Tyr | Ala | Ser | Trp | Val |
|     | 50  |     |     |     |     | 55  |     |     |     |     | 60  |     |     |     |     |

| Asn | Gly | Arg | Phe | Thr | Leu | Ser | Ser | Asp | Asn | Ala | Gln | Asn | Thr | Val | Glu |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Arg | Asp | Leu | Asp | Leu | Trp | Gly | Gln | Gly | Thr | Leu | Val | Thr | Val | Ser |
|     |     |     | 100 |     |     |     |     | 105 |     |     |     |     | 110 |     |     |

Ser

<210> SEQ ID NO 49
<211> LENGTH: 648
<212> TYPE: DNA
<213> ORGANISM: Artificial Sequence
<220> FEATURE:
<223> OTHER INFORMATION: synthesized

<400> SEQUENCE: 49

| gcccttgtga tgacccagac tccatcctcc gtgtctgcag ctgtgggagg cacagtcacc | 60 |
| atcaattgcc aggccagtca gaacatttac agcaatttag cctggtatca gcagaaacca | 120 |
| gggcagcctc ccagcctcct gatctaccag gcatccactc tggcatctgg ggtctcatcg | 180 |
| cggttcagcg gcagtggata tgggacagag ttcactctca ccatcagcga cctggagtgt | 240 |
| gccgatgctg ccacttacta ctgtcaaggc ggttattata gtgctgccct taatactttc | 300 |
| ggcggaggga ccgaggtggt ggtcaaacgt acggtggctg caccatctgt cttcatcttc | 360 |
| ccgccatctg atgagcagtt gaaatctgga actgcctctg ttgtgtgcct gctgaataac | 420 |
| ttctatccca gagaggccaa agtacagtgg aaggtggata acgccctcca atcgggtaac | 480 |
| tcccaggaga gtgtcacaga gcaggacagc aaggacagca cctacagcct cagcagcacc | 540 |
| ctgacgctga gcaaagcaga ctacgagaaa cacaaagtct acgcctgcga agtcacccat | 600 |
| cagggcctga gctcgcccgt cacaaagagc ttcaacaggg gagagtgt | 648 |

<210> SEQ ID NO 50
<211> LENGTH: 327
<212> TYPE: DNA
<213> ORGANISM: Artificial Sequence
<220> FEATURE:
<223> OTHER INFORMATION: synthesized

<400> SEQUENCE: 50

| gcccttgtga tgacccagac tccatcctcc gtgtctgcag ctgtgggagg cacagtcacc | 60 |
| atcaattgcc aggccagtca gaacatttac agcaatttag cctggtatca gcagaaacca | 120 |
| gggcagcctc ccagcctcct gatctaccag gcatccactc tggcatctgg ggtctcatcg | 180 |
| cggttcagcg gcagtggata tgggacagag ttcactctca ccatcagcga cctggagtgt | 240 |
| gccgatgctg ccacttacta ctgtcaaggc ggttattata gtgctgccct taatactttc | 300 | ggcggaggga ccgaggtggt ggtcaaa                                      327

<210> SEQ ID NO 51
<211> LENGTH: 216
<212> TYPE: PRT
<213> ORGANISM: Artificial Sequence
<220> FEATURE:
<223> OTHER INFORMATION: synthesized

<400> SEQUENCE: 51

```
Ala Leu Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Pro Pro Ser Leu Leu Ile
        35                  40                  45

Tyr Gln Ala Ser Thr Leu Ala Ser Gly Val Ser Ser Arg Phe Ser Gly
    50                  55                  60

Ser Gly Tyr Gly Thr Glu Phe Thr Leu Thr Ile Ser Asp Leu Glu Cys
65                  70                  75                  80

Ala Asp Ala Ala Thr Tyr Tyr Cys Gln Gly Gly Tyr Tyr Ser Ala Ala
                85                  90                  95

Leu Asn Thr Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 52
<211> LENGTH: 109
<212> TYPE: PRT
<213> ORGANISM: Artificial Sequence
<220> FEATURE:
<223> OTHER INFORMATION: synthesized

<400> SEQUENCE: 52

```
Ala Leu Val Met Thr Gln Thr Pro Ser Ser Val Ser Ala Ala Val Gly
 1               5                  10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Pro Pro Ser Leu Leu Ile
        35                  40                  45

Tyr Gln Ala Ser Thr Leu Ala Ser Gly Val Ser Ser Arg Phe Ser Gly
    50                  55                  60

Ser Gly Tyr Gly Thr Glu Phe Thr Leu Thr Ile Ser Asp Leu Glu Cys
65                  70                  75                  80
```

Ala Asp Ala Ala Thr Tyr Tyr Cys Gln Gly Gly Tyr Tyr Ser Ala Ala
            85                  90                  95

Leu Asn Thr Phe Gly Gly Gly Thr Glu Val Val Val Lys
            100                 105

<210> SEQ ID NO 53
<211> LENGTH: 1326
<212> TYPE: DNA
<213> ORGANISM: Artificial Sequence
<220> FEATURE:
<223> OTHER INFORMATION: synthesized

<400> SEQUENCE: 53

| | | |
|---|---|---|
| cagtcgctgg aggagtccgg gggtcgcctg gtcacgcctg gacacccct gacactcacc | 60 |
| tgcacagtct ctggattctc cctcagtagc tatgcaatga ctgggtccg ccaggctcca | 120 |
| gggaagggc tggaatacat cggatacatt ggtgatacta ctggcatagc ctacgcgagc | 180 |
| tgggcgaatg gccgattcac catctccaaa acctcgacca cggtggatct gaagatcacc | 240 |
| agtccgacaa ccggggacac ggccacctat ttctgtgcca gaggctggtc ctacttagac | 300 |
| atctggggcc aagggaccct ggtcaccgtc tcgagcgcta gcaccaaggg cccatcggtc | 360 |
| ttccccctgg cacctcctc caagagcacc tctgggggca gcggccct gggctgcctg | 420 |
| gtcaaggact acttccccga accggtgacg gtgtcgtgga actcaggcgc cctgaccagc | 480 |
| ggcgtgcaca ccttccccgc tgtcctacag tcctcaggac tctactccct cagcagcgtg | 540 |
| gtgaccgtgc cctccagcag cttgggcacc cagacctaca tctgcaacgt gaatcacaag | 600 |
| cccagcaaca ccaaggtgga caagagagtt gagcccaaat cttgtgacaa aactcacaca | 660 |
| tgcccaccgt gcccagcacc tgaactcctg ggggaccgt cagtcttcct cttcccccca | 720 |
| aaacccaagg acaccctcat gatctcccgg acccctgagg tcacatgcgt ggtggtggac | 780 |
| gtgagccacg aagaccctga ggtcaagttc aactggtacg tggacggcgt ggaggtgcat | 840 |
| aatgccaaga caaagccgcg ggaggagcag tacaacagca cgtaccgtgt ggtcagcgtc | 900 |
| ctcaccgtcc tgcaccagga ctggctgaat ggcaaggagt acaagtgcaa ggtctccaac | 960 |
| aaagccctcc cagccccat cgagaaaacc atctccaaag ccaaggca gccccgagaa | 1020 |
| ccacaggtgt acaccctgcc cccatcccgg gaggagatga ccaagaacca ggtcagcctg | 1080 |
| acctgcctgg tcaaaggctt ctatcccagc gacatcgccg tggagtggga gagcaatggg | 1140 |
| cagccggaga acaactacaa gaccacgcct cccgtgctgg actccgacgg ctccttcttc | 1200 |
| ctctatagca agctcaccgt ggacaagagc aggtggcagc aggggaacgt cttctcatgc | 1260 |
| tccgtgatgc atgaggctct gcacaaccac tacacgcaga agagcctctc cctgtctccg | 1320 |
| ggtaaa | 1326 |

<210> SEQ ID NO 54
<211> LENGTH: 336
<212> TYPE: DNA
<213> ORGANISM: Artificial Sequence
<220> FEATURE:
<223> OTHER INFORMATION: synthesized

<400> SEQUENCE: 54

| | | |
|---|---|---|
| cagtcgctgg aggagtccgg gggtcgcctg gtcacgcctg gacacccct gacactcacc | 60 |
| tgcacagtct ctggattctc cctcagtagc tatgcaatga ctgggtccg ccaggctcca | 120 |
| gggaagggc tggaatacat cggatacatt ggtgatacta ctggcatagc ctacgcgagc | 180 |
| tgggcgaatg gccgattcac catctccaaa acctcgacca cggtggatct gaagatcacc | 240 |

```
agtccgacaa ccggggacac ggccacctat ttctgtgcca gaggctggtc ctacttagac    300
atctggggcc aagggaccct ggtcaccgtc tcgagc                              336
```

<210> SEQ ID NO 55
<211> LENGTH: 442
<212> TYPE: PRT
<213> ORGANISM: Artificial Sequence
<220> FEATURE:
<223> OTHER INFORMATION: synthesized

<400> SEQUENCE: 55

```
Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Tyr Ile Gly
        35                  40                  45

Tyr Ile Gly Asp Thr Thr Gly Ile Ala Tyr Ala Ser Trp Ala Asn Gly
    50                  55                  60

Arg Phe Thr Ile Ser Lys Thr Ser Thr Val Asp Leu Lys Ile Thr
65                  70                  75                  80

Ser Pro Thr Thr Gly Asp Thr Ala Thr Tyr Phe Cys Ala Arg Gly Trp
                85                  90                  95

Ser Tyr Leu Asp Ile Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Arg Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
```

```
                340             345             350
Met Thr Lys Asn Gln Val Ser Leu Thr Cys Leu Val Lys Gly Phe Tyr
                355             360             365
Pro Ser Asp Ile Ala Val Glu Trp Glu Ser Asn Gly Gln Pro Glu Asn
                370             375             380
Asn Tyr Lys Thr Thr Pro Pro Val Leu Asp Ser Asp Gly Ser Phe Phe
385             390             395             400
Leu Tyr Ser Lys Leu Thr Val Asp Lys Ser Arg Trp Gln Gln Gly Asn
                405             410             415
Val Phe Ser Cys Ser Val Met His Glu Ala Leu His Asn His Tyr Thr
                420             425             430
Gln Lys Ser Leu Ser Leu Ser Pro Gly Lys
                435             440

<210> SEQ ID NO 56
<211> LENGTH: 112
<212> TYPE: PRT
<213> ORGANISM: Artificial Sequence
<220> FEATURE:
<223> OTHER INFORMATION: synthesized

<400> SEQUENCE: 56

Gln Ser Leu Glu Glu Ser Gly Gly Arg Leu Val Thr Pro Gly Thr Pro
1               5               10              15
Leu Thr Leu Thr Cys Thr Val Ser Gly Phe Ser Leu Ser Ser Tyr Ala
                20              25              30
Met Ser Trp Val Arg Gln Ala Pro Gly Lys Gly Leu Glu Tyr Ile Gly
                35              40              45
Tyr Ile Gly Asp Thr Thr Gly Ile Ala Tyr Ala Ser Trp Ala Asn Gly
                50              55              60
Arg Phe Thr Ile Ser Lys Thr Ser Thr Val Asp Leu Lys Ile Thr
65              70              75              80
Ser Pro Thr Thr Gly Asp Thr Ala Thr Tyr Phe Cys Ala Arg Gly Trp
                85              90              95
Ser Tyr Leu Asp Ile Trp Gly Gln Gly Thr Leu Val Thr Val Ser Ser
                100             105             110

<210> SEQ ID NO 57
<211> LENGTH: 648
<212> TYPE: DNA
<213> ORGANISM: Artificial Sequence
<220> FEATURE:
<223> OTHER INFORMATION: synthesized

<400> SEQUENCE: 57
gcccttgtga tgacccagtc tccatcctcc ctgtctgcat ctgtaggaga cagagtcacc     60
atcacttgcc aggccagtca gaacatttac agcaatttag cctggtatca gcagaaacca    120
gggaaagttc ctaagctcct gatctatcag gcctccactc tggcatctgg ggtcccatct    180
cggttcagtg gcagtggata tgggacagat ttcactctca ccatcagcag cctgcagcct    240
gaagatgttg caacttatta ctgtcaaggc ggttattata gtgctgccct taatactttc    300
ggcggaggga ccaaggtgga gatcaaacgt acggtggctg caccatctgt cttcatcttc    360
ccgccatctg atgagcagtt gaaatctgga actgcctctg ttgtgtgcct gctgaataac    420
ttctatccca gagaggccaa agtacagtgg aaggtggata acgccctcca atcgggtaac    480
tcccaggaga gtgtcacaga gcaggacagc aaggacagca cctacagcct cagcagcacc    540
```

```
ctgacgctga gcaaagcaga ctacgagaaa cacaaagtct acgcctgcga agtcacccat        600
cagggcctga gctcgcccgt cacaaagagc ttcaacaggg gagagtgt                     648
```

<210> SEQ ID NO 58
<211> LENGTH: 327
<212> TYPE: DNA
<213> ORGANISM: Artificial Sequence
<220> FEATURE:
<223> OTHER INFORMATION: synthesized

<400> SEQUENCE: 58

```
gcccttgtga tgacccagtc tccatcctcc ctgtctgcat ctgtaggaga cagagtcacc         60
atcacttgcc aggccagtca gaacatttac agcaatttag cctggtatca gcagaaacca        120
gggaaagttc ctaagctcct gatctatcag gcctccactc tggcatctgg ggtcccatct        180
cggttcagtg gcagtggata tgggacagat ttcactctca ccatcagcag cctgcagcct        240
gaagatgttg caacttatta ctgtcaaggc ggttattata gtgctgccct taatactttc        300
ggcggaggga ccaaggtgga gatcaaa                                            327
```

<210> SEQ ID NO 59
<211> LENGTH: 216
<212> TYPE: PRT
<213> ORGANISM: Artificial Sequence
<220> FEATURE:
<223> OTHER INFORMATION: synthesized

<400> SEQUENCE: 59

```
Ala Leu Val Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Val Pro Lys Leu Leu Ile
        35                  40                  45

Tyr Gln Ala Ser Thr Leu Ala Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gly Gly Tyr Tyr Ser Ala Ala
                85                  90                  95

Leu Asn Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 60
<211> LENGTH: 109
<212> TYPE: PRT
<213> ORGANISM: Artificial Sequence
<220> FEATURE:
<223> OTHER INFORMATION: synthesized

<400> SEQUENCE: 60

```
Ala Leu Val Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Val Pro Lys Leu Leu Ile
        35                  40                  45

Tyr Gln Ala Ser Thr Leu Ala Ser Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Val Ala Thr Tyr Tyr Cys Gln Gly Tyr Tyr Ser Ala Ala
                85                  90                  95

Leu Asn Thr Phe Gly Gly Gly Thr Lys Val Glu Ile Lys
            100                 105
```

<210> SEQ ID NO 61
<211> LENGTH: 1332
<212> TYPE: DNA
<213> ORGANISM: Artificial Sequence
<220> FEATURE:
<223> OTHER INFORMATION: synthesized

<400> SEQUENCE: 61

| | | | | | |
|---|---|---|---|---|---|
| gaggtgcagc | tggtggagtc | tgggggaggc | ttggtccagc | ctgggggtc | cctgagactc | 60 |
| tcctgtacag | cctctggatt | ctccctcagt | agctatgcaa | tgagctgggt | ccgccaggct | 120 |
| ccagggaagg | ggctggagta | catcggctac | attggtgata | ctactggcat | agcctacgcg | 180 |
| agctgggcga | atggcagatt | caccatctcc | aaagacaata | ccaagaacac | ggtggatctt | 240 |
| caaatgaaca | gcctgagagc | cgaggacacg | gctgtgtatt | actgtgcgag | aggctggtcc | 300 |
| tacttagaca | tctggggcca | agggaccctg | gtcaccgtct | cgagcgctag | caccaagggc | 360 |
| ccatcggtct | tccccctggc | accctcctcc | aagagcacct | ctgggggcac | agcggccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcaccc | agacctacat | ctgcaacgtg | 600 |
| aatcacaagc | ccagcaacac | caaggtggac | aagagagttg | agcccaaatc | ttgtgacaaa | 660 |
| actcacacat | gcccaccgtg | cccagcacct | gaagccgcgg | gggaccgtc | agtcttcctc | 720 |
| ttccccccaa | aacccaagga | caccctcatg | atctcccgga | cccctgaggt | cacatgcgtg | 780 |
| gtggtggacg | tgagccacga | agaccctgag | gtcaagttca | actggtacgt | ggacggcgtg | 840 |
| gaggtgcata | atgccaagac | aaagccgcgg | gaggagcagt | acaacagcac | gtaccgtgtg | 900 |
| gtcagcgtcc | tcaccgtcct | gcaccaggac | tggctgaatg | gcaaggagta | caagtgcgcg | 960 |
| gtctccaaca | aagccctccc | agcccccatc | gagaaaacca | tctccaaagc | caaagggcag | 1020 |
| ccccgagaac | cacaggtgta | caccctgccc | ccatcccggg | atgagctgac | caagaaccag | 1080 |
| gtcagcctga | cctgcctggt | caaaggcttc | tatcccagcg | acatcgccgt | ggagtgggag | 1140 |
| agcaatgggc | agccggagaa | caactacaag | accacgcctc | ccgtgctgga | ctccgacggc | 1200 |

```
tccttcttcc tctatagcaa gctcaccgtg acaagagca ggtggcagca ggggaacgtc    1260
ttctcatgct ccgtgatgca tgaggctctg cacaaccact acacgcagaa gagcctctcc    1320
ctgtctccgg gt                                                        1332
```

<210> SEQ ID NO 62
<211> LENGTH: 345
<212> TYPE: DNA
<213> ORGANISM: Artificial Sequence
<220> FEATURE:
<223> OTHER INFORMATION: synthesized

<400> SEQUENCE: 62

```
gaggtgcagc tggtggagtc tgggggaggc ttggtccagc ctgggggtc cctgagactc      60 tcctgtacag cctctggatt ctccctcagt agctatgcaa tgagctgggt ccgccaggct    120
ccagggaagg ggctggagta catcggctac attggtgata ctactggcat agcctacgcg    180
agctgggcga atggcagatt caccatctcc aaagacaata ccaagaacac ggtggatctt    240
caaatgaaca gcctgagagc cgaggacacg gctgtgtatt actgtgcgag aggctggtcc    300
tacttagaca tctggggcca agggaccctg gtcaccgtct cgagc                    345
```

<210> SEQ ID NO 63
<211> LENGTH: 444
<212> TYPE: PRT
<213> ORGANISM: Artificial Sequence
<220> FEATURE:
<223> OTHER INFORMATION: synthesized

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Lys Gly Leu Glu Tyr Ile
        35                  40                  45

Gly Tyr Ile Gly Asp Thr Thr Gly Ile Ala Tyr Ala Ser Trp Ala Asn
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Gly Trp Ser Tyr Leu Asp Ile Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
```

```
                210                 215                 220
Pro Pro Cys Pro Ala Pro Glu Ala Ala Gly Ala Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Ala
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

<210> SEQ ID NO 64
<211> LENGTH: 115
<212> TYPE: PRT
<213> ORGANISM: Artificial Sequence
<220> FEATURE:
<223> OTHER INFORMATION: synthesized

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Ala Met Ser Trp Val Arg Gln Ala Pro Gly Lys Gly Leu Glu Tyr Ile
        35                  40                  45

Gly Tyr Ile Gly Asp Thr Thr Gly Ile Ala Tyr Ala Ser Trp Ala Asn
    50                  55                  60

Gly Arg Phe Thr Ile Ser Lys Asp Asn Thr Lys Asn Thr Val Asp Leu
65                  70                  75                  80

Gln Met Asn Ser Leu Arg Ala Glu Asp Thr Ala Val Tyr Tyr Cys Ala
                85                  90                  95

Arg Gly Trp Ser Tyr Leu Asp Ile Trp Gly Gln Gly Thr Leu Val Thr
            100                 105                 110

Val Ser Ser
        115
```

<210> SEQ ID NO 65
<211> LENGTH: 654
<212> TYPE: DNA
<213> ORGANISM: Artificial Sequence
<220> FEATURE:
<223> OTHER INFORMATION: synthesized

<400> SEQUENCE: 65

```
gcctatgata tgacccagac tccatcctcc gtgtctgccg ctgtgggagg cacagtcacc    60
atcaattgcc aggccagtca gagcattaac aaccaactat cctggtatca gcagaaacca   120
gggcagcctc ccaagctcct gatctatggt gcatccactc tggcatctgg ggtcccatcg   180
cggttcaccg gcagtggatc tgggacagag ttcactctca ccatcagcgg cgtgcagtgt   240
gacgatgctg ccacttacta ctgtcatgtt cattattgca gtggtggtag ttgttttttgg   300
gctttcggcg agggaccga ggtggtggtc aaacgtacgg tggctgcacc atctgtcttc   360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca agtctacgc ctgcgaagtc   600
acccatcagg gcctgagctc gcccgtcaca aagagcttca caggggaga gtgt          654
```

<210> SEQ ID NO 66
<211> LENGTH: 333
<212> TYPE: DNA
<213> ORGANISM: Artificial Sequence
<220> FEATURE:
<223> OTHER INFORMATION: synthesized

<400> SEQUENCE: 66

```
gcctatgata tgacccagac tccatcctcc gtgtctgccg ctgtgggagg cacagtcacc    60
atcaattgcc aggccagtca gagcattaac aaccaactat cctggtatca gcagaaacca   120
gggcagcctc ccaagctcct gatctatggt gcatccactc tggcatctgg ggtcccatcg   180
cggttcaccg gcagtggatc tgggacagag ttcactctca ccatcagcgg cgtgcagtgt   240
gacgatgctg ccacttacta ctgtcatgtt cattattgca gtggtggtag ttgttttttgg   300
gctttcggcg agggaccga ggtggtggtc aaa                                 333
```

<210> SEQ ID NO 67
<211> LENGTH: 218
<212> TYPE: PRT
<213> ORGANISM: Artificial Sequence
<220> FEATURE:
<223> OTHER INFORMATION: synthesized

<400> SEQUENCE: 67

```
Ala Tyr Asp Met Thr Gln Thr Pro Ser Ser Val Ser Ala Ala Val Gly
1               5                   10                  15

Gly Thr Val Thr Ile Asn Cys Gln Ala Ser Gln Ser Ile Asn Asn Gln
            20                  25                  30

Leu Ser Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Thr Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys His Val His Tyr Cys Ser Gly Gly
```

```
              85                  90                  95
Ser Cys Phe Trp Ala Phe Gly Gly Thr Glu Val Val Lys Arg
            100                 105                 110

Thr Val Ala Ala Pro Ser Val Phe Ile Phe Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 68
<211> LENGTH: 111
<212> TYPE: PRT
<213> ORGANISM: Artificial Sequence
<220> FEATURE:
<223> OTHER INFORMATION: synthesized

<400> SEQUENCE: 68

```
Ala Tyr Asp Met Thr Gln Thr Pro Ser Ser Val Ser Ala Ala Val Gly
1               5                   10                  15

Gly Thr Val Thr Ile Asn Cys Gln Ala Ser Gln Ser Ile Asn Asn Gln
            20                  25                  30

Leu Ser Trp Tyr Gln Gln Lys Pro Gly Gln Pro Pro Lys Leu Leu Ile
        35                  40                  45

Tyr Gly Ala Ser Thr Leu Ala Ser Gly Val Pro Ser Arg Phe Thr Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys His Val His Tyr Cys Ser Gly Gly
                85                  90                  95

Ser Cys Phe Trp Ala Phe Gly Gly Gly Thr Glu Val Val Val Lys
            100                 105                 110
```

<210> SEQ ID NO 69
<211> LENGTH: 1353
<212> TYPE: DNA
<213> ORGANISM: Artificial Sequence
<220> FEATURE:
<223> OTHER INFORMATION: synthesized

<400> SEQUENCE: 69

```
caggagcagt tggaggagtc cggggggagac ctggtcaagc ctgagggatc cctgacactc      60
acctgcacag cctctggatt ctccttcagt agcagccact ggatatgctg ggtccgccag     120
gctccaggga aggggctgga gtggatcgca tgcatttata ctggtagtat tgatgtcttt     180
tactgtgcga gctgggcgaa aggccgattc accatctcca aaccctcgtc gaccacggtg     240
actctgcaaa tgcccagtct gacagccgcg gacacggcca cctatttctg tgcgagagcc     300
gctaatactg atactaccta ctttaacttg tggggcccag ggaccctcgt caccgtctcg     360
```

```
agcgctagca ccaagggccc atcggtcttc ccctggcac cctcctccaa gagcacctct      420 ggggcacag cggccctggg ctgcctggtc aaggactact ccccgaacc ggtgacggtg       480 tcgtggaact caggcgccct gaccagcggc gtgcacacct tccggctgt cctacagtcc      540 tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tatagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                 1353
```

<210> SEQ ID NO 70
<211> LENGTH: 363
<212> TYPE: DNA
<213> ORGANISM: Artificial Sequence
<220> FEATURE:
<223> OTHER INFORMATION: synthesized

<400> SEQUENCE: 70

```
caggagcagt tggaggagtc cgggggagac ctggtcaagc ctgagggatc cctgacactc       60
acctgcacag cctctggatt ctccttcagt agcagccact ggatatgctg ggtccgccag      120
gctccaggga aggggctgga gtggatcgca tgcatttata ctggtagtat tgatgtcttt      180
tactgtgcga gctgggcgaa aggccgattc accatctcca aaccctcgtc gaccacggtg      240
actctgcaag tgcccagtct gacagccgcg gacacggcca cctatttctg tgcgagagcc      300
gctaatactg atactaccta ctttaacttg tggggcccag ggaccctcgt caccgtctcg      360
agc                                                                   363
```

<210> SEQ ID NO 71
<211> LENGTH: 451
<212> TYPE: PRT
<213> ORGANISM: Artificial Sequence
<220> FEATURE:
<223> OTHER INFORMATION: synthesized

<400> SEQUENCE: 71

```
Gln Glu Gln Leu Glu Glu Ser Gly Gly Asp Leu Val Lys Pro Glu Gly
 1               5                  10                  15

Ser Leu Thr Leu Thr Cys Thr Ala Ser Gly Phe Ser Phe Ser Ser Ser
            20                  25                  30

His Trp Ile Cys Trp Val Arg Gln Ala Pro Gly Lys Gly Leu Glu Trp
        35                  40                  45

Ile Ala Cys Ile Tyr Thr Gly Ser Ile Asp Val Phe Tyr Cys Ala Ser
    50                  55                  60
```

```
Trp Ala Lys Gly Arg Phe Thr Ile Ser Lys Pro Ser Thr Thr Val
 65                  70                  75                  80

Thr Leu Gln Val Pro Ser Leu Thr Ala Ala Asp Thr Ala Thr Tyr Phe
             85                  90                  95

Cys Ala Arg Ala Ala Asn Thr Asp Thr Thr Tyr Phe Asn Leu Trp Gly
            100                 105                 110

Pro Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 72
<211> LENGTH: 121
```

<212> TYPE: PRT
<213> ORGANISM: Artificial Sequence
<220> FEATURE:
<223> OTHER INFORMATION: synthesized

<400> SEQUENCE: 72

```
Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Ser
            20                  25                  30

His Trp Ile Cys Trp Val Arg Gln Ala Pro Gly Lys Gly Leu Glu Trp
        35                  40                  45

Ile Ala Cys Ile Tyr Thr Gly Ser Ile Asp Val Phe Tyr Cys Ala Ser
    50                  55                  60

Trp Ala Lys Gly Arg Phe Thr Ile Ser Lys Pro Ser Ser Thr Thr Val
65                  70                  75                  80

Thr Leu Gln Val Pro Ser Leu Thr Ala Ala Asp Thr Ala Thr Tyr Phe
                85                  90                  95

Cys Ala Arg Ala Ala Asn Thr Asp Thr Thr Tyr Phe Asn Leu Trp Gly
            100                 105                 110

Pro Gly Thr Leu Val Thr Val Ser Ser
        115                 120
```

<210> SEQ ID NO 73
<211> LENGTH: 654
<212> TYPE: DNA
<213> ORGANISM: Artificial Sequence
<220> FEATURE:
<223> OTHER INFORMATION: synthesized

<400> SEQUENCE: 73

| gcctatgata tgacccagtc tccatcctcc ctgtctgcat ctgtaggaga cagagtcacc | 60 |
| atcaattgcc aggccagtca gagcattaac aaccaactat cctggtatca gcagaaacca | 120 |
| gggaaagttc ctaagctcct gatctatggt gcatccactc tggcatctgg ggtcccatct | 180 |
| cggttcaccg gcagtggatc tgggacagat ttcactctca ccatcagcag cctgcagcct | 240 |
| gaagatgttg caacttatta ctgtcatgtt cattattgca gtggtggtag ttgttttggg | 300 |
| gctttcggcg gagggaccaa ggtggagatc aaacgtacgg tggctgcacc atctgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca agtctacgc ctgcgaagtc | 600 |
| acccatcagg gcctgagctc gcccgtcaca aagagcttca caggggaga gtgt | 654 |

<210> SEQ ID NO 74
<211> LENGTH: 333
<212> TYPE: DNA
<213> ORGANISM: Artificial Sequence
<220> FEATURE:
<223> OTHER INFORMATION: synthesized

<400> SEQUENCE: 74

| gcctatgata tgacccagtc tccatcctcc ctgtctgcat ctgtaggaga cagagtcacc | 60 |
| atcaattgcc aggccagtca gagcattaac aaccaactat cctggtatca gcagaaacca | 120 |
| gggaaagttc ctaagctcct gatctatggt gcatccactc tggcatctgg ggtcccatct | 180 | cggttcaccg gcagtggatc tgggacagat tcactctca ccatcagcag cctgcagcct      240 gaagatgttg caacttatta ctgtcatgtt cattattgca gtggtggtag ttgttttttgg    300 gctttcggcg gagggaccaa ggtggagatc aaa                                  333

<210> SEQ ID NO 75
<211> LENGTH: 218
<212> TYPE: PRT
<213> ORGANISM: Artificial Sequence
<220> FEATURE:
<223> OTHER INFORMATION: synthesized

<400> SEQUENCE: 75

Ala Tyr Asp Met Thr Gln Ser Pro Ser Ser Leu Ser Ala Ser Val Gly
1               5                   10                  15

Asp Arg Val Thr Ile Asn Cys Gln Ala Ser Gln Ser Ile Asn Asn Gln
            20                  25                  30

Leu Ser Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His Val His Tyr Cys Ser Gly Gly
                85                  90                  95

Ser Cys Phe Trp Ala Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 76
<211> LENGTH: 111
<212> TYPE: PRT
<213> ORGANISM: Artificial Sequence
<220> FEATURE:
<223> OTHER INFORMATION: synthesized

<400> SEQUENCE: 76

Ala Tyr Asp Met Thr Gln Ser Pro Ser Ser Leu Ser Ala Ser Val Gly
1               5                   10                  15

Asp Arg Val Thr Ile Asn Cys Gln Ala Ser Gln Ser Ile Asn Asn Gln
            20                  25                  30

Leu Ser Trp Tyr Gln Gln Lys Pro Gly Lys Val Pro Lys Leu Leu Ile
        35                  40                  45

Tyr Gly Ala Ser Thr Leu Ala Ser Gly Val Pro Ser Arg Phe Thr Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His Val His Tyr Cys Ser Gly Gly
                85                  90                  95

Ser Cys Phe Trp Ala Phe Gly Gly Gly Thr Lys Val Glu Ile Lys
            100                 105                 110

<210> SEQ ID NO 77
<211> LENGTH: 1353
<212> TYPE: DNA
<213> ORGANISM: Artificial Sequence
<220> FEATURE:
<223> OTHER INFORMATION: synthesized

<400> SEQUENCE: 77
gaggtgcagc tgttggagtc tgggggaggc ttggtacagc ctggggggtc cctgagactc      60
tcctgtgcag cctctggatt cacctttagc agcagccact ggatatgctg ggtccgccag     120
gctccaggga aggggctgga gtggatcgca tgcatttata ctggtagtat tgatgtcttt     180
tactacgcga gctgggcgaa aggccggttc accatctcca gagacaattc caagaacacg     240
ctgtatctgc aaatgaacag cctgagagcc gaggacacgg ccgtatatta ctgtgcgaga     300
gccgctaata ctgatactac ctactttaac ttgtggggcc agggaaccct ggtcaccgtc     360
tcgagcgcta gcaccaaggg cccatcggtc ttccccctgg caccctcctc caagagcacc     420
tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaagccgcg     720
ggggcaccgt cagtcttcct cttcccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcgc ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctatagca agctcaccgt ggacaagagc    1260
aggtggcagc aggggaacgt cttctcatgc tccgtgatgc atgaggctct gcacaaccac    1320
tacacgcaga agagcctctc cctgtctccg ggt                                 1353

<210> SEQ ID NO 78
<211> LENGTH: 366
<212> TYPE: DNA
<213> ORGANISM: Artificial Sequence
<220> FEATURE:
<223> OTHER INFORMATION: synthesized

<400> SEQUENCE: 78
gaggtgcagc tgttggagtc tgggggaggc ttggtacagc ctggggggtc cctgagactc      60
tcctgtgcag cctctggatt cacctttagc agcagccact ggatatgctg ggtccgccag     120

```
gctccaggga aggggctgga gtggatcgca tgcatttata ctggtagtat tgatgtcttt    180
tactacgcga gctgggcgaa aggccggttc accatctcca gagacaattc caagaacacg    240
ctgtatctgc aaatgaacag cctgagagcc gaggacacgg ccgtatatta ctgtgcgaga    300
gccgctaata ctgatactac ctactttaac ttgtggggcc agggaaccct ggtcaccgtc    360
tcgagc                                                                366
```

<210> SEQ ID NO 79
<211> LENGTH: 451
<212> TYPE: PRT
<213> ORGANISM: Artificial Sequence
<220> FEATURE:
<223> OTHER INFORMATION: synthesized

<400> SEQUENCE: 79

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
                20                  25                  30

His Trp Ile Cys Trp Val Arg Gln Ala Pro Gly Lys Gly Leu Glu Trp
            35                  40                  45

Ile Ala Cys Ile Tyr Thr Gly Ser Ile Asp Val Phe Tyr Tyr Ala Ser
        50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ala Ala Asn Thr Asp Thr Thr Tyr Phe Asn Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Ala Ala
225                 230                 235                 240

Gly Ala Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
305                 310                 315                 320
Gly Lys Glu Tyr Lys Cys Ala Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 80
<211> LENGTH: 122
<212> TYPE: PRT
<213> ORGANISM: Artificial Sequence
<220> FEATURE:
<223> OTHER INFORMATION: synthesized

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
                20                  25                  30

His Trp Ile Cys Trp Val Arg Gln Ala Pro Gly Lys Gly Leu Glu Trp
            35                  40                  45

Ile Ala Cys Ile Tyr Thr Gly Ser Ile Asp Val Phe Tyr Tyr Ala Ser
50                  55                  60

Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ala Ala Asn Thr Asp Thr Thr Tyr Phe Asn Leu Trp
            100                 105                 110

Gly Gln Gly Thr Leu Val Thr Val Ser Ser
            115                 120
```

ANTI-PD-1 ANTIBODIES AND METHODS OF MAKING AND USING THEREOF

CROSS REFERENCE TO RELATED APPLICATIONS

This application claims the benefit of U.S. Provisional Patent Application No. 62/545,603 filed Aug. 15, 2017, U.S. Provisional Patent Application No. 62/524,553 filed Jun. 25, 2017, U.S. Provisional Patent Application No. 62/524,554 filed Jun. 25, 2017, U.S. Provisional Patent Application No. 62/524,557 filed Jun. 25, 2017, and U.S. Provisional Patent Application No. 62/524,558 filed Jun. 25, 2017, which application is expressly incorporated herein by reference in its entirety.

TECHNICAL FIELD

The present application generally relates to the technical field of antibodies, and more particularly relates to making and using anti-PD-1 antibodies.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

Cancerous tumours can adopt a variety of mechanisms to avoid detection and/or destruction by the host immune system. One method utilized by a variety of tumours is to suppress the immune T-cell response by the expression of PD-1 on the surface of tumour cells. When the PD-1 engages its receptor PD-1 on the surface of T-cells, a negative co-stimulatory signal is sent into the T-cell that results in the suppression of the T-cell. In this manner tumour cells are able to avoid a T-cell mediated response of the host immune system.

Pharmaceutical agents that are able to bind to PD-1 and block the negative co-stimulatory signal from suppressing the T-cell response have been shown to increase the host immune response to cancerous tumours and have resulted in a beneficial response for cancer patients (see Iwai et al. J. Biomed. Sci. 24:26 (2017)).

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals that further influence the response of the T-cells. A secondary positive signal is required for full T-cell activation ((Lafferty et al., Ausl. J. Exp. Biol. Med. Sci. 53: 27-42 (1975)). Negative secondary signals can result in T-cell suppression and tolerance.

Programmed death 1 (PD-1) is a member of the CD28 family of receptors and is expressed on T-cells and other cell types. PD-1 is one of the routes used by to transmit negative secondary signals into T-cells. PD-1 is a cell-surface ligand glycoprotein for PD-1 that was shown to downregulate T-cell activation upon binding to PD-1 (Freeman et al. J. Exp. Med. 192: 1027-34 (2000)). PD-1, also known as B7-H1 or CD274, is a 40 kDa type 1 transmembrane protein that has been shown to be expressed in several human cancers and is associated with increased tumour aggressiveness and an increased risk of death (Thomson et al. PNAS 101: 17174-9 (2004)). PD-1 expression in cancers is thought to suppress the immune response to tumours via suppression of T-cells via its interaction with PD-1 (Dong et al. Nat. Med. 8: 793-800 (2002)). Consequently, several PD-1 inhibitors are currently being developed or have been developed to enhance T-cell activity against tumours for the treatment of cancer.

While pharmaceutical agents that are able to bind to PD-1 and block the negative co-stimulatory signal from suppressing the T-cell response have been shown to increase the host immune response to cancerous tumours and have resulted in a beneficial response for cancer patients (see Iwai et al. J. Biomed. Sci. 24:26 (2017)), it remains unclear what is the optimal PD-1 binding site(s) and relevant affinity for developing the most effective and tumour cell-specific anti-PD-1 antibodies for cancer treatment.

SUMMARY

In one aspect, the application provides anti-PD-1 monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

In one embodiment, an isolated monoclonal antibody (mAb) or antigen-binding fragment thereof that binds specifically to human PD-1 is provided. In one embodiment, the isolated mAb or antigen-binding fragment comprises an amino acid sequence having a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, or SEQ ID NO:80. The percentage homology is not less than 70%, 80%, 90%, 95%, 98% or 99%.

In one embodiment, the isolated mAb or antigen-binding fragment has a binding affinity to human PD-1 with a Kd not greater than 3-nM, 40 nM, 50 nM, 60 nM, 70 nM, 80 nM, 90 nM, or 100 nM.

In one embodiment, the isolated mAb or antigen-binding fragment may exhibit one or more functional properties including without limitation high affinity binding to human PD-1, inhibiting binding of human PD-L1 to PD-1, enhancing T cell activation, stimulating antibody response, reversing the suppressive function of an immunosuppressive cell, or a combination thereof. In one embodiment, the immunosuppressive cell comprises a regulatory cell. In one embodiment, the isolated mAb or antigen-binding fragment may enhance T-cell activation via mechanisms or pathways including T-cell proliferation, IFN-γ and/or IL-2 secretion, or a combination thereof.

In one embodiment, the isolated mAb or antigen-binding fragment comprises a human framework region. In one embodiment, the isolated mAb or antigen-binding fragment is a humanized antibody, a chimeric antibody, or a recombinant antibody.

In one embodiment, the isolated mAb or antigen-binding fragment is an IgG. In one embodiment, the antigen-binding fragment is a Fv, a Fab, a F(ab')2, a scFV or a scFV2 fragment. In one embodiment, the isolated mAb is a bispecific antibody, tri-specific antibody, or multi-specific antibody.

In one embodiment, the application provides an isolated mAb or antigen-binding fragment that has an IgG1 heavy chain with an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, or SEQ ID NO:79. The percentage homology is not less than 70%, 80%, 90%, 95%, 98% or 99%.

In one embodiment, the application provides an isolated mAb or antigen-binding fragment that has a kappa light chain having an amino acid sequence having a percentage homology SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, or SEQ ID NO:75. The percentage homology is not less than 70%, 80%, 90%, 95%, 98% or 99%.

In one embodiment, the application provides an isolated mAb or antigen-binding fragment that has a variable light chain having an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, or SEQ ID NO:76. The percentage homology is not less than 70%, 80%, 90%, 95%, 98% or 99%.

In one embodiment, the application provides an isolated mAb or antigen-binding fragment that has a variable heavy chain having an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, or SEQ ID NO:80. The percentage homology is not less than 70%, 80%, 90%, 95%, 98% or 99%.

In one embodiment, isolated nucleic acids are provided that encode at least a portion of the isolated mAb or antigen-binding fragment disclosed herein. In some embodiments, the isolated nucleic acid encodes an amino acid having a percentage homology with: 1) the IgG1 heavy chain having the sequence of SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, or SEQ ID NO:79; 2) the kappa light chain having the sequence of SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, or SEQ ID NO:75; 3) the variable light chain having the sequence of SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, or SEQ ID NO:76; and 4) the variable heavy chain having a sequence of SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, or SEQ ID NO:80. The percentage homology is not less than 70%, 80%, 90%, 95%, 98% or 99%.

In one embodiment, an expression vector is provided comprising the isolated nucleic acid that encodes an amino acid sequence disclosed herein. In one embodiment, the expression vector is expressible in a cell.

In one embodiment, the application provides a host cell comprising nucleic acids that encode an amino acid sequence disclosed herein. In one embodiment, the application provides a host cell comprising the expression vector that comprises one or more of nucleic acids that encode an amino acid sequence disclosed herein. In one embodiment, the host cell can be a prokaryotic cell or a eukaryotic cell.

In another aspect, the application provides methods for producing an antibody. In one embodiment, the method comprises the step of using the host cell described above. The method includes the steps of providing a host cell that contains an expression vector expressible in the host cell, the expression vector comprises nucleic acids encoding at least a portion of the isolated mAb or antigen-binding fragment, or peptides disclosed herein, to produce an antibody by the expression of the nucleic acids.

The application further provides immuno-conjugates including a drug unit or an imaging agent linked to the mAb or antigen-binding fragments disclosed herein. The immuno-conjugate may include a drug unit and an isolated mAb or antigen-binding fragment disclosed herein.

The linker may be cleavable or non-cleavable. In one embodiment, the linker comprises an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly(ethylene glycol) linker.

In one embodiment, the drug unit in the immuno-conjugate is a chemotherapeutic agent, a growth inhibitory agent, a toxin, or a radioactive isotope. In one embodiment, the drug unit comprises a cytotoxic agent from class of calicheamicin, an antimitotic agent, or a combination thereof. In one embodiment, the drug unit comprises, ozogamicin, monomethyl auristatin E, emtansine, a derivative or a combination thereof.

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof. In one embodiment, the immune regulatory reagents activate or suppress immune cells, T cell, NK cell, B cell, macrophage, or dendritic cell.

In one embodiment, the imaging agent may be radionuclide, a florescent agent, a quantum dots, or a combination thereof.

The application further provides pharmaceutical compositions. In one embodiment, the pharmaceutical composition includes the isolated mAb or antigen-binding fragment disclosed herein and a pharmaceutically acceptable carrier. In one embodiment, the pharmaceutical composition provides the immuno-conjugate disclosed herein and pharmaceutically acceptable carrier.

In one embodiment, the pharmaceutical composition further comprises a chemotherapeutic agent, a growth inhibitory agent, a drug unit from class of calicheamicin, an antimitotic agent, a toxin, a radioactive isotope, a therapeutic agent, or a combination thereof. In one embodiment, the therapeutic agent comprises an antibody, a chemotherapy agent, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

In one embodiment, a method of treating a subject with a cancer is provided, comprising administering to the subject an effective amount of the isolated mAb or antigen-binding fragment disclosed herein. In one embodiment, the method includes directly injecting into the tumour site an effective amount of the monoclonal antibodies, the antigen-binding fragment thereof, and the immuno-conjugates and disclosed herein.

In one embodiment, the cancer has cells that express PD-1. In one embodiment, the cancer may be breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

In one embodiment, the method of treating a subject with a cancer may further include co-administering an effective amount of a therapeutic agent. In one embodiment, the therapeutic agent comprises an antibody, an enzyme, or a combination thereof. In one embodiment, the therapeutic agent can include a chemotherapeutic agent, a growth inhibitory agent, a drug unit from class of calicheamicin, an antimitotic agent, a radioactive isotope, a toxin, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In one embodiment, the therapeutic agent comprises a check point inhibitor.

In one embodiment, the therapeutic agent may include capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

In some embodiments, the subject receiving treatment is a human. In one embodiment, a solution is provided that comprises an effective concentration of the isolated mAb or an antigen-binding fragment disclosed herein, wherein the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

Preferred embodiments according to the present application may now be described with reference to the FIGUREs, in which like reference numerals denote like elements.

FIG. 1 shows an example of the PD-1 binding ELISA performed on the supernatants from a B cell culture plate. Shaded wells indicate wells that were identified as positive for anti-PD-1 antibodies.

DETAILED DESCRIPTION

Figure 2:
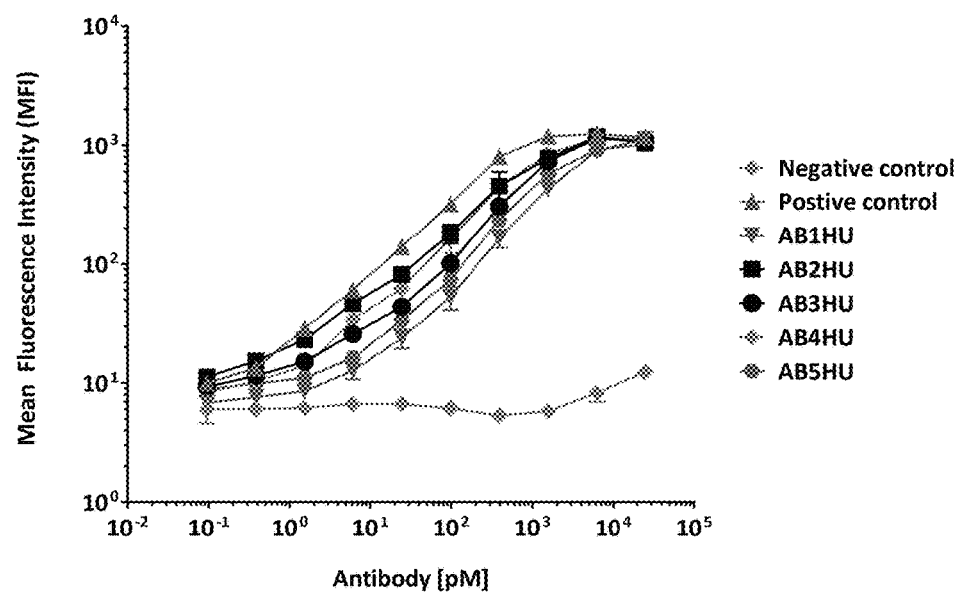
FIG. 2 is an example of bio-layer interferometry analysis of the ability of an antibody supernatant to block the association between PD-1 to PD-1. The black trace utilizes a blocking antibody supernatant whereas the gray trace is with a non-blocking antibody supernatant

The application provides, among others, isolated antibodies, their antigen-binding fragments, methods of making such antibodies or fragments, bispecific or multi-specific molecules, antibody-drug conjugates and/or immuno-conjugates composed from such antibodies or antigen binding fragments, pharmaceutical compositions containing the antibodies, bispecific or multi-specific molecules, antibody-drug conjugates and/or immuno-conjugates and methods for treating cancers using the mAbs and their antigen-binding fragments disclosed herein.

In one aspect, the application provides isolated monoclonal antibodies or their antigen-binding fragments having a binding specificity to human PD-1. The antibodies or their antigen-binding fragments may exhibit one or more desirable functional properties, such as high affinity binding to PD-1, the ability to inhibit binding of PD-1 to PD-L1, the ability to enhance T cell activation including proliferation, IFN-γ and/or IL-2 secretion, the ability to stimulate antibody responses and/or the ability to reverse the suppressive function of immunosuppressive cells, such as T regulatory cells. In one embodiment, the antibodies or their antigen-binding fragments may be derived from specific heavy and light chain amino acid sequences and/or structural features such as complementarity determining regions (CDRs) composed of specific amino acid sequences.

The term "antibody" is used in the broadest sense and specifically covers single monoclonal antibodies (including agonist and antagonist antibodies), antibody compositions with polyepitopic specificity, as well as antibody fragments (e.g., Fab, F(ab')$_2$, and Fv), so long as they exhibit the desired biological activity. In some embodiments, the antibody may be monoclonal, polyclonal, chimeric, single chain, bispecific or bi-effective, human and humanized antibodies as well as active fragments thereof. Examples of active fragments of molecules that bind to known antigens include Fab, F(ab')$_2$, scFv and Fv fragments, including the products of a Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site with the immunological binding specificity to an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by the hybridoma method first described by Kohler & Milstein, *Nature*, 256:495 (1975), or may be made by recombinant DNA methods (see, e.g., U.S. Pat. No. 4,816,567).

In one embodiment, the monoclonal antibodies herein may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011). In the present application, antibodies were created by the immunization of rabbits with both human PD-1 protein and cells transiently expressing human PD-1 on the cell surface. Rabbits are known to create antibodies of high affinity, diversity and specificity (Weber et al. Exp. Mol. Med. 49:e305). B cells from immunized animals were cultured in vitro and screened for the production of anti-PD-1 antibodies. The antibody variable genes were isolated using recombinant DNA techniques and the resulting antibodies were expressed recombinantly and further screened for desired features such as ability to inhibit the binding of PD-1 to PD-1, the ability to bind to non-human primate PD-1 and the ability to enhance human T-cell activation. This general method of antibody discovery is similar to that described in Seeber et al. PLOS One. 9:e86184 (2014).

The term "antigen-or epitope-binding portion or fragment" refers to fragments of an antibody that are capable of binding to an antigen (PD-1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen-or epitope-binding fragments" can be derived from an antibody of the present application by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')$_2$ fragment that has two antigen combining sites and is still capable of cross-linking antigen.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda ($\lambda$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)). A "humanized antibody" may also be obtained by a novel genetic engineering approach that enables production of affinity-matured humanlike polyclonal antibodies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present application to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. In some embodiments, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the application may be caused for instance by addition, deletion, substitution, insertion or recombination.

In another aspect, the application provides pharmaceutical compositions including the antibodies, the antigen-binding fragments, and the immuno-conjugates thereof. Formulation of the pharmaceutical composition can be accomplished according to standard methodology know to those of ordinary skill in the art.

The antibodies according to the application can be prepared in a physiologically acceptable formulation and may comprise a pharmaceutically acceptable carrier, diluent and/or excipient using known techniques. For example, the antibody according to the application and as described herein including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio. Formulation of the pharmaceutical composition according to the application can be accomplished according to standard methodology know to those of ordinary skill in the art.

In another aspect, the application provides methods for treating a subject using anti-PD-1 antibodies or other molecules disclosed herein. In one embodiment, the method may be used to inhibit growth of tumor cells. In one embodiment, the method may be used to stimulate a protective autoimmune response, to modify an immune response or to stimulate antigen-specific immune responses. In one embodiment, the method includes the step of administering to a subject in need of such treatment an effective amount of the mAB, the antigen-binding fragments, or composition disclosed herein.

The compositions may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. In general, the composition may be administered by topical, oral, rectal, nasal, interdermal, intraperitoneal, or parenteral (for example, intravenous, subcutaneous, or intramuscular) routes. In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

In one embodiment, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

A sustained release matrix, as used herein, is a matrix made of materials, usually polymers which are degradable by enzymatic or acid/base hydrolysis or by dissolution. Once inserted into the body, the matrix is acted upon by enzymes and body fluids. The sustained release matrix desirably is chosen by biocompatible materials such as liposomes, polylactides (polylactide acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

It is well known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

The composition may be administered in combination with other compositions comprising a biologically active substance or compound. Example biologically active substances or compounds include without limitation compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, "atypical antipsychotics" such as, for example clozapine, ziprasidone, risperidone, aripiprazole or olanzapine or cholinesterase inhibitors (ChEIs) such as tacrine, rivastigmine, donepezil, and/or galantamine and other drugs and nutritive supplements such as, for example, vitamin B12, cysteine, a precursor of acetylcholine, lecithin, choline, Ginkgo biloba, acetyl-L-carnitine, idebenone, propentofylline, or a xanthine derivative, together with an antibody according to the present application and, optionally, a pharmaceutically acceptable carrier and/or a diluent and/or an excipient and instructions for the treatment of diseases.

The pharmaceutical composition may further comprise proteinaceous carriers such as, for example, serum albumin or immunoglobulin, particularly of human origin. Further biologically active agents may be present in the pharmaceutical composition of the application dependent on the intended use. Proteinaceous pharmaceutically active matter may be present in amounts between 1 ng and 10 mg per dose. Generally, the regime of administration should be in the range of between 0.1 µg and 10 mg of the antibody according to the application, particularly in a range 1.0 µg to 1.0 mg, and more particularly in a range of between 1.0 µg and 100 µg, with all individual numbers falling within these ranges also being part of the application. If the administration occurs through continuous infusion a more proper dosage may be in the range of between 0.01 µg and 10 mg units per kilogram of body weight per hour with all individual numbers falling within these ranges also being part of the application.

The present application may be understood more readily by reference to the following detailed description of specific embodiments included herein. Although the present application has been described with reference to specific details

EXAMPLES

Example 1

Generation of Anti-PD-1 Antibodies

Monoclonal antibodies against human PD-1 were developed by immunizing New Zealand white rabbits. The initial immunizations were with 100 µg of recombinant human PD-1 extracellular domain mixed 1:1 v/v with Complete Freund's Adjuvant performed by subcutaneous injection. Subsequent boosts were performed at weeks 3, 6, and 8 with 50 µg of antigen in Incomplete Freund's Adjuvant. In addition to antigen, on weeks 3, 6 and 8 the animals were also boosted with $1 \times 10^6$ HEK-293 cells which were transiently transfected to express full-length human PD-1.

On week 8 the serum from the animals was tested for anti-PD-1 titer by ELISA. 96-well plates were coated overnight by passive adsorption at 4° C. with goat anti-rabbit IgG antibody (Jackson ImmunoResearch). The coated wells were washed and blocked with 1% milk for 1 hour at room temperature followed by a 1 hour room temperature incubation with human PD-1 extracellular domain human Fc domain fusion protein. After washing, undiluted serum is added to the wells and serially diluted 1:10 across the plate over a total of 7 wells each. After a 1 hour incubation at room temperature the plates were washed and then incubated with a goat anti-human IgG Fc-specific horseradish peroxidase-conjugated antibody (Jackson ImmunoResearch). The plates were washed and then incubated with Ultra TMB Substrate (Fisher Scientific) for 30 minutes at room temperature. The signal in the wells was detected by an absorbance plate reader at 450 nm wave length to generate a titer curve. The anti-PD-1 titer is compared to an ELISA performed with serum from the same animal that was obtained prior to immunization.

On week 9, Rabbits with significant anti-PD-1 titers were selected for harvest and the generation of monoclonal antibodies.

B-cells from anti-PD-1 positive rabbits were harvested from the spleen and lymph nodes at week 12 following the initial immunization. The B cells were cultured for one week in 96-well plates to allow their differentiation into plasma cells and for secretion of antibodies. The supernatants from these plasma cell cultures were screened by ELISA as described above for the presence of PD-1-specific antibodies as shown in FIG. 1.

B cells secreting anti-PD-1 antibodies were isolated from positive wells using a magnetic capture method. Briefly, streptavidin magnetic beads (ThermoFisher Scientific) were coated with biotin-conjugated human PD-1 extracellular domain protein. The coated beads were incubated with the cells from an anti-PD-1 positive well. The bead cell complexes were washed using a magnet to remove any non-specific cells and the bead cell complexes were added directly to a tube containing an RT-PCR master mix.

The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasmids generated from each well were transiently co-transfected into HEK-293 cells to produce rabbit/human chimeric antibodies. The resulting supernatants containing the recombinant antibodies were clarified by centrifugation.

Recombinant antibody supernatants were confirmed to contain anti-PD-1 antibodies using bio-layer interferometry analysis on a ForteBio Octet Red 96 instrument. Anti-human Fc biosensors (Pall ForteBio) were used to capture antibodies in the supernatants. Association to PD-1 was observed by real-time interferometry by placing the biosensors in wells containing recombinant human PD-1 extracellular domain protein. Dissociation was measured after transfer of the biosensors into wells containing 10× kinetics buffer (Pall ForteBio). The software provided by the manufacturer was used to analyze the interferometry data.

Humanized forms for anti-PD-1 antibodies AB1-AB5 were produced and are indicated by an appended "HU" following their original designation. For example AB1HU is the humanized form of antibody AB1.

Example 2

Binding Affinities of Anti-PD-1 Antibodies

The binding kinetics of selected anti-PD-1 antibodies AB1-AB5 and AB1HU-AB5HU was determined by bio-layer interferometry analysis on a ForteBio Octet Red 96 instrument. First, purified antibodies were produced by protein A chromatography using HEK-293 transiently-transfected antibody supernatants. This assay was performed by immobilizing the purified antibodies to anti-human Fc biosensors. PD-1 binding to and dissociation from the biosensors was then observed at various concentrations of PD-1. Specifically, eight anti-human Fc biosensors were placed into wells containing the same purified antibody for 5 minutes. Biosensors were equilibrated in kinetics buffer (Pall ForteBio) for 1 minute to establish a baseline. Association of PD-1 was observed by placing the biosensors into wells containing various concentrations of human PD-1 extracellular domain for 5 minutes. Dissociation was measured after transfer of the biosensors into kinetics buffer and monitoring the interferometry signals for 15 minutes. All steps of the assay were performed at 30° C. with shaking at 1000 RPM. The on and off rates (kon and koff) and the equilibrium binding constant KD were determined using the software provided by the manufacturer and were fit using a 1:1 binding global fit model comprising several of the concentrations tested. Results of the kinetic studies are presented in TABLE 1.

TABLE 1

| Ab | KD [M] | Kon [1/Ms] | Koff [1/s] |
|---|---|---|---|
| AB1 | 4.80E−09 | 3.60E+04 | 1.60E−04 |
| AB1HU | 1.60E−08 | 1.20E+04 | 2.00E−04 |
| AB2 | 8.60E−08 | 6.70E+04 | 5.70E−03 |
| AB2HU | 1.70E−08 | 8.90E+04 | 1.50E−03 |
| AB3 | 9.00E−10 | 1.30E+05 | 1.20E−04 |
| AB3HU | 1.10E−09 | 1.30E+05 | 1.40E−04 |
| AB4 | 9.20E−09 | 1.10E+05 | 1.00E−03 |

TABLE 1-continued

| Ab | KD [M] | Kon [1/Ms] | Koff [1/s] |
|---|---|---|---|
| AB4HU | 4.30E−09 | 8.70E+04 | 3.80E−04 |
| AB5 | 3.30E−09 | 7.80E+04 | 2.60E−04 |
| AB5HU | 6.60E−09 | 6.10E+04 | 4.00E−04 |

Example 3

Antibodies Binding to Cell-Surface Expressed PD-1

The human PD-1 gene was subcloned into the pcDNA3.1 mammalian expression vector and transfected into the Jurkat human T cell line. A clonal cell population expressing high levels of huPD-1 was generated by G418 drug selection and single-cell sorting. This Jurkat/huPD-1 clonal cell line was labeled with FVS520 viability dye (BD Biosciences, 1:2000 dilution) for 15 minutes at room temperature. The labeled cells were then diluted in FACS buffer (2% FBS in PBS), added to V-bottom 96-well plates (50,000 cells per well), and stained with 0-25 nM anti-huPD1 or isotype control antibody on ice for 30 minutes. Cells were washed to remove excess primary antibody, then labeled with Alexa luor 647-conjugated goat anti-human Fc secondary antibody (Jackson Immunoresearch, 1:1600 dilution) on ice for 20 minutes. The labeled cells were then washed with FACS buffer before acquisition on a BD FACSCalibur flow cytometer equipped with the Cytek AMS plate loader system. AB1HU-AB5HU results in this assay are shown in FIG. 2. Data points show the median fluorescence intensity (MFI) on the AF647 channel after gating on live cells. Nonlinear regression methods were used to fit curves to each data set, and error bars represent the standard deviation of duplicate samples.

Example 4

Antibody-Mediated Blocking of huPD-1/huPD-L1 Interactions

Figure 3:
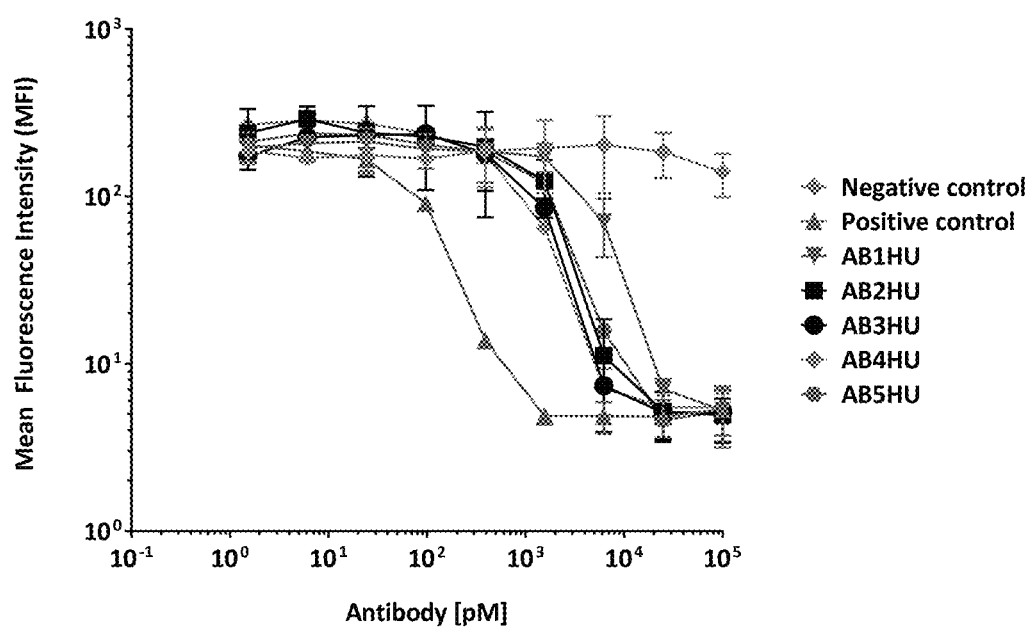
FIG. 3 shows bio-layer interferometry analysis of the ability of antibodies AB6-AB10 to block the association between PD-1 to PD-1. Shown starting from PD-1 binding followed by baseline followed by PD-1 binding. Neg. Control is an anti-PD-1 antibody which can bind to PD-1 but does not block the association between PD-1 to PD-1.

The Jurkat/huPD-1 clonal cell line was labeled with FVS520 viability dye (BD Biosciences, 1:2000 dilution) for 15 minutes at room temperature. The labeled cells were then diluted in FACS buffer (2% FBS in PBS), added to V-bottom 96-well plates (50,000 cells per well), and stained with 0-100 nM anti-huPD1 or isotype control antibody on ice for 30 minutes. Cells were washed to remove excess antibody, then labeled with 15 ug/ml His-tag purified, monobiotinylated huPD-1 on ice for 30 minutes. Cells were washed again with FACS buffer, then labeled with 0.25 ug/ml APC-conjugated streptavidin on ice for 20 minutes. Cells were washed again with before acquisition on a BD FACSCalibur flow cytometer equipped with the Cytek AMS plate loader system. AB1HU-AB5HU results in this assay are shown in FIG. 3. and show the median fluorescence intensity (MFI) on the APC channel after gating on live cells. Error bars represent the standard deviation of duplicate samples.

Example 5

Antibody-Mediated Blocking of huPD-1/huPD-12 Interactions

The Jurkat/huPD-1 clonal cell line was labeled with FVS520 viability dye (BD Biosciences, 1:2000 dilution) for 15 minutes at room temperature. The labeled cells were then diluted in FACS buffer (2% FBS in PBS), added to V-bottom 96-well plates (50,000 cells per well), and stained with 0-100 nM anti-huPD1 or isotype control antibody on ice for 30 minutes. Cells were washed to remove excess antibody, then labeled with 15 ug/ml His-tag purified, monobiotinylated huPD-L2 on ice for 30 minutes. Cells were washed with FACS buffer, then labeled with 0.25 ug/ml APC-conjugated streptavidin on ice for 20 minutes. Cells were washed again with FACS buffer before acquisition on a FACSCalibur flow cytometer equipped with the Cytek AMS plate loader system. AB1HU-AB5HU results in this assay are shown in FIG. 7. Data show the median fluorescence intensity (MFI) on the APC channel after gating on live cells. Error bars represent the standard deviation of duplicate samples.

Example 6

Effect of PD-1 Antibodies on Human T Cell Activation

Figure 4:
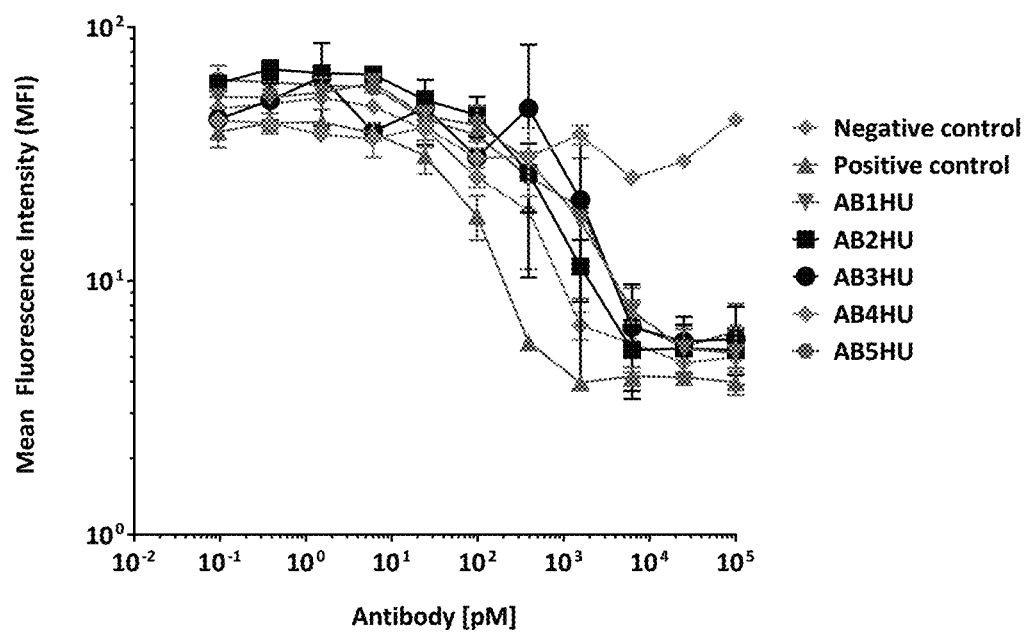
FIG. 4 is an example of binding kinetics data for two anti-PD-1 antibodies binding to PD-1. The data shown is for the 5 minute association followed by the 15 minute dissociation for various concentrations of PD-1.
Figure 5:
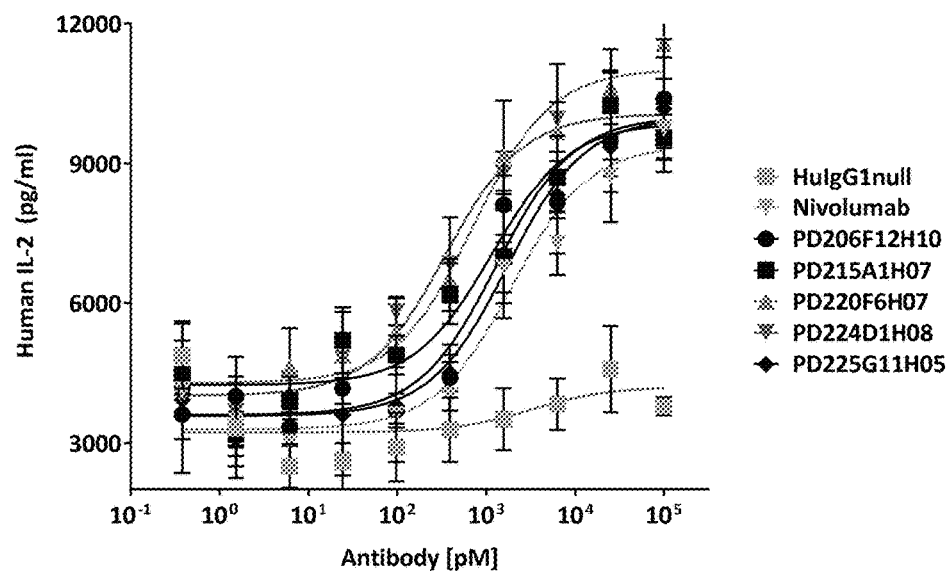
FIG. 5 shows humanized antibodies binding to cell-surface expressed PD-1. Data points show the median fluorescence intensity (MFI) on the AF647 channel after gating on live cells. Nonlinear regression methods were used to fit curves to each data set, and error bars represent the standard deviation of duplicate samples.

Human PBMCs (100,000 cells/well) from a healthy donor were combined with 100 ng/ml superantigen (staphylococcal enterotoxin B (SEB), Toxin Technology, Inc.) and 0-100 nM anti-huPD1 or isotype control antibody in complete RPMI media in flat-bottom 96-well plates. The assay plates were incubated in a 37° C., 5% CO2 incubator for 3 days, then supernatant samples were tested for the presence of huIL-2 using a commercially available kit (R&D Systems). AB1HU-AB5HU results in this assay are shown in FIG. 4. Data points represent the huIL-2 values for the antibodies tested, which were interpolated from a standard ELISA curve. Nonlinear regression methods were used to fit curves to each data set, and error bars represent the standard deviation of quadruplicate samples.

While the application has been particularly shown and described as referenced to the embodiments thereof, those skilled in the art will understand that the foregoing and other changes in form and detail may be made therein without departing from the spirit and scope. All references cited or referred to in this application are hereby incorporated by reference in their entireties.

SEQUENCE LISTING

SI-11 ANTI-PD-1 ANTIBODY SEQUENCES
SEQ ID NO: 1
AB1 CHIMERIC LIGHT CHAIN FULL-LENGTH NUCLEOTIDE SEQUENCE
CAAGTGCTGACCCAGACTGCATCGTCCGTGTCTGCAGCTGTGGGAGGCACAGTCACCATCAGTTGCCAGTCCAGTC
AGAGTGTTTATGATAACAACTGGTTAGCCTGGTATCAGCAGAAACCAGGGCAGCCTCCCATGCTCCTGATCTATAC
AGTATCCACTCTGGCATCTGGGGTCTCATCGCGGTTCAAAGGCAGTGGATCTGGGACACAGTTCACTCTCACCATC
AGCGGCGTGCAGTGTGACGATGCTGCCACTTACTACTGTCAAGGCACTTATTATAGTAGTGGTTGGAACTTTGCTT
TCGGCGGAGGGACCGAGGTGGTGGTCAAACGTACGGTGGCTGCACCATCTGTCTTCATCTTCCCGCCATCTGATG
AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT
ACAGCCTCAGCAGCACCCTGACGCTGAGCAAAGCAGACTACGAGAAACACAAAGTCTACGCCTGCGAAGTCACCC
ATCAGGGCCTGAGCTCGCCCGTCACAAAGAGCTTCAACAGGGGAGAGTGT

SEQ ID NO: 2
AB1 CHIMERIC LIGHT CHAIN VARIABLE LIGHT CHAIN NUCLEOTIDE SEQUENCE
CAAGTGCTGACCCAGACTGCATCGTCCGTGTCTGCAGCTGTGGGAGGCACAGTCACCATCAGTTGCCAGTCCAGTC
AGAGTGTTTATGATAACAACTGGTTAGCCTGGTATCAGCAGAAACCAGGGCAGCCTCCCATGCTCCTGATCTATAC
AGTATCCACTCTGGCATCTGGGGTCTCATCGCGGTTCAAAGGCAGTGGATCTGGGACACAGTTCACTCTCACCATC
AGCGGCGTGCAGTGTGACGATGCTGCCACTTACTACTGTCAAGGCACTTATTATAGTAGTGGTTGGAACTTTGCTT
TCGGCGGAGGGACCGAGGTGGTGGTCAAA

SEQ ID NO: 3
AB1 CHIMERIC LIGHT CHAIN FULL-LENGTH AMINO ACID SEQUENCE. HUMAN KAPPA CONSTANT
DOMAIN IS UNDERLINED
QVLTQTASSVSAAVGGTVTISCQSSQSVYDNNWLAWYQQKPGQPPMLLIYTVSTLASGVSSRFKGSGSGTQFTLTISGV
QCDDAATYYCQGTYYSSGWNFAFGGGTEVVVK<u>RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC</u>

SEQ ID NO: 4
AB1 CHIMERIC LIGHT CHAIN VARIABLE LIGHT CHAIN AMINO ACID SEQUENCE. COMPIMENTARITY
DETERMINING REGIONS ARE UNDERLINED
QVLTQTASSVSAAVGGTVTISC<u>QSSQSVYDNNWLA</u>WYQQKPGQPPMLLIY<u>TVSTLAS</u>GVSSRFKGSGSGTQFTLTISGV
QCDDAATYYC<u>QGTYYSSGWNFA</u>FGGGTEVVVK

SEQ ID NO: 5
AB1 CHIMERIC HEAVY CHAIN FULL-LENGTH NUCLEOTIDE SEQUENCE
CAGTCGTTGGAGGAGTCCGGGGGAGACCTGGTCAAGCCTGAGGGATCCCTGACACTCACCTGCAAAGCCTCTGG
ATTCGACTTCAGTAGCGGCTACTGGATATGCTGGGTCCGCCAGGCTCCAGGGAAGGGGCTGGAGTTGATCGCATG
CATTTATGCTGGTACTAGTGGTAGTACTTCCTACGCGAGCTGGGCGAGAGGCCGATTCACCATCTCCGAAACCTCG
TCGACCACGGTGACTCTGCAAATGACCAGTCTGACAGCCGCGGACTCGGCCACCTATTTCTGTGCGAGAAATCTTT
ACACTTACAATAGCTTGTGGGGCCAGGGCACCCTGGTCACCGTCTCGAGCTAGCACCAAGGGCCCATCGGTCT
TCCCCCTGGCACCCTCCTCCAAGAGCACCTCTGGGGGCACAGCGGCCCTGGGCTGCCTGGTCAAGGACTACTTCC
CGAACCGGTGACGGTGTCGTGGAACTCAGGCGCCCTGACCAGCGGCGTGCACACCTTCCCGGCTGTCCTACAGTC
CTCAGGACTCTACTCCCTCAGCAGCGTGGTGACCGTGCCCTCCAGCAGCTTGGGCACCCAGACCTACATCTGCAAC
GTGAATCACAAGCCCAGCAACACCAAGGTGGACAAGAGAGTTGAGCCCAAATCTTGTGACAAAACTCACACATGC
CCACCGTGCCCAGCACCTGAACTCCTGGGGGGACCGTCAGTCTTCCTCTTCCCCCCAAAACCCAAGGACACCCTCA
TGATCTCCCGGACCCCTGAGGTCACATGCGTGGTGGTGGACGTGAGCCACGAAGACCCTGAGGTCAAGTTCAACT
GGTACGTGGACGGCGTGGAGGTGCATAATGCCAAGACAAAGCCGCGGGAGGAGCAGTACAACAGCACGTACCG
TGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGA
CATCGCCGTGGAGTGGGAGAGCAATGGGCAGCCGGAGAACAACTACAAGACCACGCCTCCCGTGCTGGACTCCG
ACGGCTCCTTCTTCCTCTATAGCAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTCTCCGGGTAAA

SEQ ID NO: 6
AB1 CHIMERIC HEAVY CHAIN VARIABLE HEAVY CHAIN NUCLEOTIDE SEQUENCE
CAGTCGTTGGAGGAGTCCGGGGGAGACCTGGTCAAGCCTGAGGGATCCCTGACACTCACCTGCAAAGCCTCTGG
ATTCGACTTCAGTAGCGGCTACTGGATATGCTGGGTCCGCCAGGCTCCAGGGAAGGGGCTGGAGTTGATCGCATG
CATTTATGCTGGTACTAGTGGTAGTACTTCCTACGCGAGCTGGGCGAGAGGCCGATTCACCATCTCCGAAACCTCG
TCGACCACGGTGACTCTGCAAATGACCAGTCTGACAGCCGCGGACTCGGCCACCTATTTCTGTGCGAGAAATCTTT
ACACTTACAATAGCTTGTGGGGCCAGGGCACCCTGGTCACCGTCTCGAGC

SEQ ID NO: 7
AB1 CHIMERIC HEAVY CHAIN FULL-LENGTH AMINO ACID SEQUENCE. HUMAN GAMMA-1 CONSTANT
DOMAIN IS UNDERLINED
QSLEESGGDLVKPEGSLTLTCKASGFDFSSGYWICWVRQAPGKGLELIACIYAGTSGSTSYASWARGRFTISETSSTTVTL
QMTSLTAADSATYFCARNLYTYNSLWGQGTLVTVSS<u>ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK</u>

SEQ ID NO: 8
AB1 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGDLVKPEGSLTLTCKASGEDFSS<u>GYWIC</u>WVRQAPGKGLELIA<u>CIYAGTSGSTSYASWA</u>RGRFTISETSSTTVTL
QMTSLTAADSATYFCAR<u>NLYTYNSL</u>WGQGTLVTVSS

SEQ ID NO: 9
AB1HU HUMANIZED LIGHT CHAIN FULL-LENGTH NUCLEOTIDE SEQUENCE
GACATCCAGATGACCCAGTCTCCTTCCACCCTGTCTGCATCTGTAGGAGACAGAGTCACCATCACTTGCCAGTCCA
GTCAGAGTGTTTATGATAACAACTGGTTAGCCTGGTATCAGCAGAAACCAGGGAAAGCCCCTAAGCTCCTGATCTA
TACAGTATCCACTCTGGCATCTGGGGTCCCATCAAGGTTCAGCGGCAGTGGATCTGGGACAGAATTCACTCTCACC
ATCAGCAGCCTGCAGCCTGATGATTTTGCAACTTATTACTGCCAAGGCACTTATTATAGTAGTGGTTGGAACTTTGC
TTTCGGCGGAGGGACCAAGGTGGAGATCAAACGTACGGTGGCTGCACCATCTGTCTTCATCTTCCCGCCATCTGAT

GAGCAGTTGAAATCTGGAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGACAGCAAGGACAGCACC
TACAGCCTCAGCAGCACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGT

SEQ ID NO: 10
AB1HU HUMANIZED LIGHT CHAIN VARIABLE LIGHT CHAIN NUCLEOTIDE SEQUENCE
GACATCCAGATGACCCAGTCTCCTTCCACCCTGTCTGCATCTGTAGGAGACAGAGTCACCATCACTTGCCAGTCCA
GTCAGAGTGTTTATGATAACAACTGGTTAGCCTGGTATCAGCAGAAACCAGGGAAAGCCCCTAAGCTCCTGATCTA
TACAGTATCCACTCTGGCATCTGGGGTCCCATCAAGGTTCAGCGGCAGTGGATCTGGGACAGAATTCACTCTCACC
ATCAGCAGCCTGCAGCCTGATGATTTTGCAACTTATTACTGCCAAGGCACTTATTATAGTAGTGGTTGGAACTTTGC
TTTCGGCGGAGGGACCAAGGTGGAGATCAAA

SEQ ID NO: 11
AB1HU HUMANIZED LIGHT CHAIN FULL-LENGTH AMINO ACID SEQUENCE. HUMAN KAPPA CONSTANT
DOMAIN IS UNDERLINED
DIQMTQSPSTLSASVGDRVTITCQSSQSVYDNNWLAWYQQKPGKAPKLLIYTVSTLASGVPSRFSGSGSGTEFTLTISSL
QPDDFATYYCQGTYYSSGWNFAFGGGTKVEIK<u>RTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRGEC</u>

SEQ ID NO: 12
AB1HU HUMANIZED LIGHT CHAIN VARIABLE LIGHT CHAIN AMINO ACID SEQUENCE.
COMPLEMENTARITY DETERMINING REGIONS ARE UNDERLINED
DIQMTQSPSTLSASVGDRVTITC<u>QSSQSVYDNNWLA</u>WYQQKPGKAPKLLIY<u>TVSTLAS</u>GVPSRFSGSGSGTEFTLTISSL
QPDDFATYYC<u>QGTYYSSGWNFA</u>FGGGTKVEIK

SEQ ID NO: 13
AB1HU HUMANIZED HEAVY CHAIN FULL-LENGTH NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTC
TGGATTCGACTTCAGTAGCGGCTACTGGATATGCTGGGTCCGCCAGGCTCCAGGGAAGGGGCTGGAGTTGATCGC
ATGCATTTATGCTGGTACTAGTGGTAGTACTTCCTACGCGAGCTGGGCGAGAGGCAGATTCACCATCTCCGAAACC
TCCAAGAACACGGTGACTCTTCAAATGAACAGCCTGAGAGCCGAGGACTCGGCTGTGTATTACTGTGCGAGAAAT
CTTTACACTTACAATAGCTTGTGGGGCCAGGGAACCCTGGTCACCGTCTCGAGCGCTAGCACCAAGGGCCCATCG
GTCTTCCCCCTGGCACCCTCCTCCAAGAGCACCTCTGGGGGCACAGCGGCCCTGGGCTGCCTGGTCAAGGACTACT
TCCCCGAACCGGTGACGGTGTCGTGGAACTCAGGCGCCCTGACCAGCGGCGTGCACACCTTCCCGGCTGTCCTAC
AGTCCTCAGGACTCTACTCCCTCAGCAGCGTGGTGACCGTGCCCTCCAGCAGCTTGGGCACCCAGACCTACATCTG
CAACGTGAATCACAAGCCCAGCAACACCAAGGTGGACAAGAGAGTTGAGCCCAAATCTTGTGACAAAACTCACAC
ATGCCCACCGTGCCCAGCACCTGAAGCCGCGGGGGCACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGT
ACCGTGTGGTCAGCGTCCTCACCGTCCTGCACCAGGACTGGCTGAATGGCAAGGAGTACAAGTGCAAGGTCTCCA
ACAAAGCCCTCCCAGCCCCCATCGAGAAAACCATCTCCAAAGCCAAAGGGCAGCCCCGAGAACCACAGGTGTACA
CCCTGCCCCCATCCCGGGATGAGCTGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACGCCTCCCGTGCTGGACT
CCGACGGCTCCTTCTTCCTCTATAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCGGGT

SEQ ID NO: 14
AB1HU HUMANIZED HEAVY CHAIN VARIABLE HEAVY CHAIN NUCLEOTIDE SEQUENCE
GAGGTGCAGCTGGTGGAGTCTGGGGGAGGCTTGGTCCAGCCTGGGGGGTCCCTGAGACTCTCCTGTGCAGCCTC
TGGATTCGACTTCAGTAGCGGCTACTGGATATGCTGGGTCCGCCAGGCTCCAGGGAAGGGGCTGGAGTTGATCGC
ATGCATTTATGCTGGTACTAGTGGTAGTACTTCCTACGCGAGCTGGGCGAGAGGCAGATTCACCATCTCCGAAACC
TCCAAGAACACGGTGACTCTTCAAATGAACAGCCTGAGAGCCGAGGACTCGGCTGTGTATTACTGTGCGAGAAAT
CTTTACACTTACAATAGCTTGTGGGGCCAGGGAACCCTGGTCACCGTCTCGAGC

SEQ ID NO: 15
AB1HU HUMANIZED HEAVY CHAIN FULL-LENGTH AMINO ACID SEQUENCE. HUMAN GAMMA1
CONSTANT DOMAIN IS UNDERLINED
EVQLVESGGGLVQPGGSLRLSCAASGFDFSSGYWICWVRQAPGKGLELIACIYAGTSGSTSYASWARGRFTISETSKNTV
TLQMNSLRAEDSAVYYCARNLYTYNSLWGQGTLVTVSS<u>ASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKRVEPKSCDKTHTCPPCPAPEAAGAP
SVFLFPPKPKDTLMISRTPEVTCVVVDVSHEDPEVKFNWYVDGVEVHNAKTKPREEQYNSTYRVVSVLTVLHQDWLNG
KEYKCAVSNKALPAPIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG</u>

SEQ ID NO: 16
AB1HU HUMANIZED HEAVY CHAIN VARIABLE HEAVY CHAIN AMINO ACID SEQUENCE.
COMPLEMENTARITY DETERMINING REGIONS ARE UNDERLINED
EVQLVESGGGLVQPGGSLRLSCAASGEDFS<u>SGYWIC</u>WVRQAPGKGLELIA<u>CIYAGTSGSTSYASWARG</u>RFTISETSKNTV
TLQMNSLRAEDSAVYYCAR<u>NLYTYNSLW</u>GQGTLVTVSS

SEQ ID NO: 17
AB2 CHIMERIC LIGHT CHAIN FULL-LENGTH NUCLEOTIDE SEQUENCE
GATGTTGTGATGACCCAGACTCCAGCCTCCGTGTCTGCAGTTGTGGGAGGCACAGTCACCATCAAGTGCCAGGCC
AGTCAGAGCATTTACAGCTACTTAAACTGGTATCAGCAGAAACCAGGGCAGCCTCCCAAGCTCCTGATCTATGGTG
CATCCAATCTGGCATCTGGGGTCTCATCGCGATTCAAAGGCAGTGGATCTGGGACAGAGTTCACTCTCACCATCAG
CGACCTGGAGTGTGCCGATGCTGCCACTTACTACTGTCAATGTAGTTGGTTGAGTGGTGCTGTTGGTAATGCTTTC

```
GGCGGAGGGACCGAGGTGGTGGTCAAACGTACGGTGGCTGCACCATCTGTCTTCATCTTCCCGCCATCTGATGAG
CAGTTGAAATCTGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGACAGCACCTAC
AGCCTCAGCAGCACCCTGACGCTGAGCAAAGCAGACTACGAGAAACACAAAGTCTACGCCTGCGAAGTCACCCAT
CAGGGCCTGAGCTCGCCCGTCACAAAGAGCTTCAACAGGGGAGAGTGT

SEQ ID NO: 18
AB2 CHIMERIC LIGHT CHAIN VARIABLE LIGHT CHAIN NUCLEOTIDE SEQUENCE
GATGTTGTGATGACCCAGACTCCAGCCTCCGTGTCTGCAGTTGTGGGAGGCACAGTCACCATCAAGTGCCAGGCC
AGTCAGAGCATTTACAGCTACTTAAACTGGTATCAGCAGAAACCAGGGCAGCCTCCCAAGCTCCTGATCTATGGTG
CATCCAATCTGGCATCTGGGGTCTCATCGCGATTCAAAGGCAGTGGATCTGGGACAGAGTTCACTCTCACCATCAG
CGACCTGGAGTGTGCCGATGCTGCCACTTACTACTGTCAATGTAGTTGGTTGAGTGGTGCTGTTGGTAATGCTTTC
GGCGGAGGGACCGAGGTGGTGGTCAAA

SEQ ID NO: 19
AB2 CHIMERIC LIGHT CHAIN FULL-LENGTH AMINO ACID SEQUENCE. HUMAN KAPPA CONSTANT
DOMAIN IS UNDERLINED
DVVMTQTPASVSAVVGGTVTIKCQASQSIYSYLNWYQQKPGQPPKLLIYGASNLASGVSSRFKGSGSGTEFTLTISDLEC
ADAATYYCQCSWLSGAVGNAFGGGTEVVVK<u>RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC</u>

SEQ ID NO: 20
AB2 CHIMERIC LIGHT CHAIN VARIABLE LIGHT CHAIN AMINO ACID SEQUENCE. COMPIMENTARITY
DETERMINING REGIONS ARE UNDERLINED
DVVMTQTPASVSAVVGGTVTIKCQ<u>ASQSIYSYLN</u>WYQQKPGQPPKLLIY<u>GASNLAS</u>GVSSRFKGSGSGTEFTLTISDLEC
ADAATYYCQ<u>CSWLSGAVGNA</u>FGGGTEVVVK

SEQ ID NO: 21
AB2 CHIMERIC HEAVY CHAIN FULL-LENGTH NUCLEOTIDE SEQUENCE
CAGGAGCAACTGTGGAGTCCGGGGAGGCCTGGTCCAGCCTGAGGGATCCTGACACTCACCTGCACAGCTTCT
GGATTCTCCTTCAGTAGCTACTGGATGTGCTGGGTCCGCCAGGCTCCAGGGAAGGGGCTGGAGTGGATCGGATG
CATTACGACTGGTAGTGGTAGCACTTACTACGCGAGCTGGGCGAAGCGCCGATTCACCATCTCCAAAACCTCGTCG
ACCACGGTGACTCTGCAAATGACCAGTCTGACAGCCGCGGACACGGCCACCTATTTCTGTACGAGAGCATTTGACT
TGTGGGGCCCGGGGACCCTGGTCACCGTCTCGAGCGCTAGCACCAAGGGCCCATCGGTCTTCCCCCTGGCACCCT
CCTCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTACTC
CCTCAGCAGCGTGGTGACCGTGCCCTCCAGCAGCTTGGGCACCCAGACCTACATCTGCAACGTGAATCACAAGCCC
AGCAACACCAAGGTGGACAAGAGAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACCCTCATGATCTCCCGGACCCC
TGAGGTCACATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGCTCCTTCTTCCTC
TATAGCAAGCTCACCGTGGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAA

SEQ ID NO: 22
AB2 CHIMERIC HEAVY CHAIN VARIABLE HEAVY CHAIN NUCLEOTIDE SEQUENCE
CAGGAGCAACTGTGGAGTCCGGGGAGGCCTGGTCCAGCCTGAGGGATCCTGACACTCACCTGCACAGCTTCT
GGATTCTCCTTCAGTAGCTACTGGATGTGCTGGGTCCGCCAGGCTCCAGGGAAGGGGCTGGAGTGGATCGGATG
CATTACGACTGGTAGTGGTAGCACTTACTACGCGAGCTGGGCGAAGCGCCGATTCACCATCTCCAAAACCTCGTCG
ACCACGGTGACTCTGCAAATGACCAGTCTGACAGCCGCGGACACGGCCACCTATTTCTGTACGAGAGCATTTGACT
TGTGGGGCCCGGGGACCCTGGTCACCGTCTCGAGC

SEQ ID NO: 23
AB2 CHIMERIC HEAVY CHAIN FULL-LENGTH AMINO ACID SEQUENCE. HUMAN GAMMA-1 CONSTANT
DOMAIN IS UNDERLINED
QEQLVESGGGLVQPEGSLTLTCTASGFSFSSYWMCWVRQAPGKGLEWIGCITTGSGSTYYASWAKRRFTISKTSSTTVT
LQMTSLTAADTATYFCTRAFDLWGPGTLVTVSS<u>ASTKGPSVFPLAPSSKSTSGGTAALGCLVKDYFPEPVTVSWNSGAL
TSGVHTFPAVLQSSGLYSLSSVVTVPSSSLGTQTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPGK</u>

SEQ ID NO: 24
AB2 CHIMERIC HEAVY CHAIN VARIABLE HEAVY CHAIN AMINO ACID SEQUENCE. COMPLIMENTARITY
DETERMINING REGIONS ARE UNDERLINED
QEQLVESGGGLVQPEGSLTLTCTASGFSFS<u>SYWMC</u>WVRQAPGKGLEWIG<u>CITTGSGSTYYASWAK</u>RRFTISKTSSTTVT
LQMTSLTAADTATYFCTR<u>AFDL</u>WGPGTLVTVSS

SEQ ID NO: 25
AB2HU HUMANIZED LIGHT CHAIN FULL-LENGTH NUCLEOTIDE SEQUENCE
GACATCCAGATGACCCAGTCTCCATCCTCCCTGTCTGCATCTGTAGGAGACAGAGTCACCATCACTTGCCAGGCCA
GTCAGAGCATTTACAGCTACTTAAACTGGTATCAGCAGAAACCAGGGAAAGCCCCTAAGCTCCTGATCTATGGTGC
ATCCAATCTGGCATCTGGGGTCCCATCAAGGTTCAGTGGCAGTGGATCTGGGACAGATTTCACTCTCACCATCAGC
```

| SEQUENCE LISTING |
| --- |
| AGTCTGCAACCTGAAGATTTTGCAACTTACTACTGTCAAAGCAGTTGGTTGAGTGGTGCTGTTGGTAATGCTTTCG
GCGGAGGGACCAAGGTGGAGATCAAACGTACGGTGGCTGCACCATCTGTCTTCATCTTCCCGCCATCTGATGAGC
AGTTGAAATCTGGAACTGCCTCTGTTGTGTGCCTGCTGAATAACTTCTATCCCAGAGAGGCCAAAGTACAGTGGAA
GGTGGATAACGCCCTCCAATCGGGTAACTCCCAGGAGAGTGTCACAGAGCAGGACAGCAAGGACAGCACCTACA
GCCTCAGCAGCACCCTGACGCTGAGCAAAGCAGACTACGAGAAACACAAAGTCTACGCCTGCGAAGTCACCCATC
AGGGCCTGAGCTCGCCCGTCACAAAGAGCTTCAACAGGGGAGAGTGT

SEQ ID NO: 26
AB2HU HUMANIZED LIGHT CHAIN VARIABLE LIGHT CHAIN NUCLEOTIDE SEQUENCE
GACATCCAGATGACCCAGTCTCCATCCTCCCTGTCTGCATCTGTAGGAGACAGAGTCACCATCACTTGCCAGGCCA
GTCAGAGCATTTACAGCTACTTAAACTGGTATCAGCAGAAACCAGGGAAAGCCCCTAAGCTCCTGATCTATGGTGC
ATCCAATCTGGCATCTGGGGTCCCATCAAGGTTCAGTGGCAGTGGATCTGGGACAGATTTCACTCTCACCATCAGC
AGTCTGCAACCTGAAGATTTTGCAACTTACTACTGTCAAAGCAGTTGGTTGAGTGGTGCTGTTGGTAATGCTTTCG
GCGGAGGGACCAAGGTGGAGATCAAA

SEQ ID NO: 27
AB2HU HUMANIZED LIGHT CHAIN FULL-LENGTH AMINO ACID SEQUENCE. HUMAN KAPPA CONSTANT
DOMAIN IS UNDERLINED
DIQMTQSPSSLSASVGDRVTITCQASQSIYSYLNWYQQKPGKAPKLLIYGASNLASGVPSRFSGSGSGTDFTLTISSLQPE
DFATYYCQSSWLSGAVGNAFGGGTKVEIK<u>RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC</u>

SEQ ID NO: 28
AB2HU HUMANIZED LIGHT CHAIN VARIABLE LIGHT CHAIN AMINO ACID SEQUENCE.
COMPLEMENTARITY DETERMINING REGIONS ARE UNDERLINED
DIQMTQSPSSLSASVGDRVTITCQ<u>ASQSIYSYLN</u>WYQQKPGKAPKLLIY<u>GASNLAS</u>GVPSRFSGSGSGTDFTLTISSLQPE
DFATYYC<u>QSSWLSGAVGNA</u>FGGGTKVEIK

SEQ ID NO: 29
AB2HU HUMANIZED HEAVY CHAIN FULL-LENGTH NUCLEOTIDE SEQUENCE
CAGGAGCAGCTGTTGGAGTCTGGGGGAGGCTTGGTACAGCCTGGGGGGTCCCTGAGACTCTCCTGTACAGCCTCT
GGATTCTCCTTTAGCAGCTACTGGATGTGCTGGGTCCGCCAGGCTCCAGGGAAGGGGCTGGAGTGGATCGGATG
CATTACGACTGGTAGTGGTAGCACTTACTACGCGAGCTGGGCGAAGCGCCGGTTCACCATCTCCAAAGACAATTCC
AAGAACACGGTGACTCTGCAAATGAACAGCCTGAGAGCCGAGGACACGGCCGTATATTACTGTACGAGAGCATTT
GACTTGTGGGGCCAGGGAACCCTGGTCACCGTCTCGAGCGCTAGCACCAAGGGCCCATCGGTCTTCCCCCTGGCA
CCCTCCTCCAAGAGCACCTCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAGACCTACATCTGCAACGTGAATCACAA
GCCCAGCAACACCAAGGTGGACAAGAGAGTTGAGCCCAAATCTTGTGACAAAACTCACACATGCCCACCGTGCCC
AGCACCTGAAGCCGCAGGGGCACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGTGGA
CGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCGCGGTCTCCAACAAAGCCCTCCCA
GCCCCCATCGAGAAAACCATCTCCAAAGCCAAAGGGCAGCCCCGAGAACCACAGGTGTACACCCTGCCCCCATCC
CGGGATGAGCTGACCAAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGACTCCGACGGCTCCTT
CTTCCTCTATAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGT

SEQ ID NO: 30
AB2HU HUMANIZED HEAVY CHAIN VARIABLE HEAVY CHAIN NUCLEOTIDE SEQUENCE
CAGGAGCAGCTGTTGGAGTCTGGGGGAGGCTTGGTACAGCCTGGGGGGTCCCTGAGACTCTCCTGTACAGCCTCT
GGATTCTCCTTTAGCAGCTACTGGATGTGCTGGGTCCGCCAGGCTCCAGGGAAGGGGCTGGAGTGGATCGGATG
CATTACGACTGGTAGTGGTAGCACTTACTACGCGAGCTGGGCGAAGCGCCGGTTCACCATCTCCAAAGACAATTCC
AAGAACACGGTGACTCTGCAAATGAACAGCCTGAGAGCCGAGGACACGGCCGTATATTACTGTACGAGAGCATTT
GACTTGTGGGGCCAGGGAACCCTGGTCACCGTCTCGAGC

SEQ ID NO: 31
AB2HU HUMANIZED HEAVY CHAIN FULL-LENGTH AMINO ACID SEQUENCE. HUMAN GAMMA1
CONSTANT DOMAIN IS UNDERLINED
QEQLLESGGGLVQPGGSLRLSCTASGFSFSSYWMCWVRQAPGKGLEWIGCITTGSGSTYYASWAKRRFTISKDNSKNT
VTLQMNSLRAEDTAVYYCTRAFDLWGQGTLVTVSS<u>ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPKSCDKTHTCPPCPAPEAAGAPSV
FLFPPKPKDTLMISRTPEVTCVVVDVSHEDPEVKFNWYVDGVEVHNAKTKPREEQYNSTYRVVSVLTVLHQDWLNGKE
YKCAVSNKALPAPIEKTISKAKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPG</u>

SEQ ID NO: 32
AB2HU HUMANIZED HEAVY CHAIN VARIABLE HEAVY CHAIN AMINO ACID SEQUENCE.
COMPLEMENTARITY DETERMINING REGIONS ARE UNDERLINED
QEQLLESGGGLVQPGGSLRLSCTASGFSFS<u>SYWMC</u>WVRQAPGKGLEWIG<u>CITTGSGSTYYASWAKR</u>RFTISKDNSKNT
VTLQMNSLRAEDTAVYYCTR<u>AFDL</u>WGQGTLVTVSS

SEQ ID NO: 33
AB3 CHIMERIC LIGHT CHAIN FULL-LENGTH NUCLEOTIDE SEQUENCE
CAAGTGCTGACCCAGACTCCATCTCCCGTGTCTGCAGCTGTGGGAGGCACAGTCAGCATCAGTTGCCAGTCCAGTC
CGAGTGTTTATAGTAACTACTTATCCTGGTTTCAGCAGAAACCAGGGCAGCCTCCCAAGCTCCTGATCTATTATGCA

```
TCCACTCTGGCATCTGGGGTCCCTTCGCGGTTCAAAGGCAGTGGATCTGGGACACAGTTCACTCTCACCATCAGCG
ACGTGCAGTGTGACGATGCTGCCACTTACTACTGTGCAGGCGGTTATAGTAGTAGTACTCGTGCTTTCGGCGGAG
GGACCGAGGTGGTGGTCAAACGTACGGTGGCTGCACCATCTGTCTTCATCTTCCCGCCATCTGATGAGCAGTTGAA
ATCTGGAACTGCCTCTGTTGTGTGCCTGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTCACCCATCAGGGCCTG
AGCTCGCCCGTCACAAAGAGCTTCAACAGGGGAGAGTGT

SEQ ID NO: 34
AB3 CHIMERIC LIGHT CHAIN VARIABLE LIGHT CHAIN NUCLEOTIDE SEQUENCE
CAAGTGCTGACCCAGACTCCATCTCCCGTGTCTGCAGCTGTGGGAGGCACAGTCAGCATCAGTTGCCAGTCCAGTC
CGAGTGTTTATAGTAACTACTTATCCTGGTTTCAGCAGAAACCAGGGCAGCCTCCCAAGCTCCTGATCTATTATGCA
TCCACTCTGGCATCTGGGGTCCCTTCGCGGTTCAAAGGCAGTGGATCTGGGACACAGTTCACTCTCACCATCAGCG
ACGTGCAGTGTGACGATGCTGCCACTTACTACTGTGCAGGCGGTTATAGTAGTAGTACTCGTGCTTTCGGCGGAG
GGACCGAGGTGGTGGTCAAA

SEQ ID NO: 35
AB3 CHIMERIC LIGHT CHAIN FULL-LENGTH AMINO ACID SEQUENCE. HUMAN KAPPA CONSTANT
DOMAIN IS UNDERLINED
QVLTQTPSPVSAAVGGTVSISCQSSPSVYSNYLSWFQQKPGQPPKLLIYYASTLASGVPSRFKGSGSGTQFTLTISDVQCD
DAATYYCAGGYSSSTRAFGGGTEVVVK<u>RTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC</u>

SEQ ID NO: 36
AB3 CHIMERIC LIGHT CHAIN VARIABLE LIGHT CHAIN AMINO ACID SEQUENCE. COMPIMENTARITY
DETERMINING REGIONS ARE UNDERLINED
QVLTQTPSPVSAAVGGTVSISC<u>QSSPSVYSNYLS</u>WFQQKPGQPPKLLIY<u>YASTLAS</u>GVPSRFKGSGSGTQFTLTISDVQCD
DAATYYC<u>AGGYSSSTRA</u>FGGGTEVVVK

SEQ ID NO: 37
AB3 CHIMERIC HEAVY CHAIN FULL-LENGTH NUCLEOTIDE SEQUENCE
CAGGAGCAGGTGAAGGAGACCGGGGGAGGCCTGGTCCAGCCTGGGGGATCCCTGACACTCTCCTGCAAAGCCTC
TGGATTTACCATCAGTAGCTATGGAGTGAGCTGGGTCCGCCAGGCTCCAGGGAAGGGGCTGGAGTGGATCGCAT
TGATTTTTCCTGGTATTGGTTTCAAAGACTACGCGAGCTGGGTGAATGGCCGATTCACCCTCTCCAGCGACAACGC
CCAGAACACTGTGGAACTTCAGATGAACAGTCTGACAGCGGCGGACACGGCCGCCTATTTCTGTGCGAGAGATTT
GGACTTGTGGGGCCAAGGGACCCTCGTCACCGTCTCGAGCGCTAGCACCAAGGGCCCATCGGTCTTCCCCCTGGC
ACCCTCCTCCAAGAGCACCTCTGGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGACTCCGACGGCTCCTT
CTTCCTCTATAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAA

SEQ ID NO: 38
AB3 CHIMERIC HEAVY CHAIN VARIABLE HEAVY CHAIN NUCLEOTIDE SEQUENCE
CAGGAGCAGGTGAAGGAGACCGGGGGAGGCCTGGTCCAGCCTGGGGGATCCCTGACACTCTCCTGCAAAGCCTC
TGGATTTACCATCAGTAGCTATGGAGTGAGCTGGGTCCGCCAGGCTCCAGGGAAGGGGCTGGAGTGGATCGCAT
TGATTTTTCCTGGTATTGGTTTCAAAGACTACGCGAGCTGGGTGAATGGCCGATTCACCCTCTCCAGCGACAACGC
CCAGAACACTGTGGAACTTCAGATGAACAGTCTGACAGCGGCGGACACGGCCGCCTATTTCTGTGCGAGAGATTT
GGACTTGTGGGGCCAAGGGACCCTCGTCACCGTCTCGAGC

SEQ ID NO: 39
AB3 CHIMERIC HEAVY CHAIN FULL-LENGTH AMINO ACID SEQUENCE. HUMAN GAMMA-1 CONSTANT
DOMAIN IS UNDERLINED
QEQVKETGGGLVQPGGSLTLSCKASGFTISSYGVSWVRQAPGKGLEWIALIFPGIGFKDYASWVNGRFTLSSDNAQNT
VELQMNSLTAADTAAYFCARDLDLWGQGTLVTVSS<u>ASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK</u>

SEQ ID NO: 40
AB3 CHIMERIC HEAVY CHAIN VARIABLE HEAVY CHAIN AMINO ACID SEQUENCE. COMPLIMENTARITY
DETERMINING REGIONS ARE UNDERLINED
QEQVKETGGGLVQPGGSLTLSCKASGFTIS<u>SYGVS</u>WVRQAPGKGLEWIA<u>LIFPGIGFKDYASWVNG</u>RFTLSSDNAQNT
VELQMNSLTAADTAAYFCAR<u>DLDL</u>WGQGTLVTVSS
```

SEQUENCE LISTING

SEQ ID NO: 41
AB3HU HUMANIZED LIGHT CHAIN FULL-LENGTH NUCLEOTIDE SEQUENCE
GACATCCAGATGACCCAGTCTCCATCCTCCCTGTCTGCATCTGTAGGAGACAGAGTCACCATCACTTGCCAGTCCA
GTCCGAGTGTTTATAGTAACTACTTATCCTGGTATCAGCAGAAACCAGGGAAAGTTCCTAAGCTCCTGATCTATTAT
GCATCCACTCTGGCATCTGGGGTCCCATCTCGGTTCAGTGGCAGTGGATCTGGGACAGATTTCACTCTCACCATCA
GCAGCCTGCAGCCTGAAGATGTTGCAACTTATTACTGTGCAGGCGGTTATAGTAGTAGTACTCGTGCTTTCGGCGG
AGGGACCAAGGTGGAGATCAAACGTACGGTGGCTGCACCATCTGTCTTCATCTTCCCGCCATCTGATGAGCAGTTG
AAATCTGGAACTGCCTCTGTTGTGTGCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGACAGCAAGGACAGCACCTACAGCCTC
AGCAGCACCCTGACGCTGAGCAAAGCAGACTACGAGAAACACAAAGTCTACGCCTGCGAAGTCACCCATCAGGGC
CTGAGCTCGCCCGTCACAAAGAGCTTCAACAGGGGAGAGTGT

SEQ ID NO: 42
AB3HU HUMANIZED LIGHT CHAIN VARIABLE LIGHT CHAIN NUCLEOTIDE SEQUENCE
GACATCCAGATGACCCAGTCTCCATCCTCCCTGTCTGCATCTGTAGGAGACAGAGTCACCATCACTTGCCAGTCCA
GTCCGAGTGTTTATAGTAACTACTTATCCTGGTATCAGCAGAAACCAGGGAAAGTTCCTAAGCTCCTGATCTATTAT
GCATCCACTCTGGCATCTGGGGTCCCATCTCGGTTCAGTGGCAGTGGATCTGGGACAGATTTCACTCTCACCATCA
GCAGCCTGCAGCCTGAAGATGTTGCAACTTATTACTGTGCAGGCGGTTATAGTAGTAGTACTCGTGCTTTCGGCGG
AGGGACCAAGGTGGAGATCAAA

SEQ ID NO: 43
AB3HU HUMANIZED LIGHT CHAIN FULL-LENGTH AMINO ACID SEQUENCE. HUMAN KAPPA CONSTANT
DOMAIN IS UNDERLINED
DIQMTQSPSSLSASVGDRVTITCQSSPSVYSNYLSWYQQKPGKVPKLLIYYASTLASGVPSRFSGSGSGTDFTLTISSLQPE
DVATYYCAGGYSSSTRAFGGGTKVEIK<u>RTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC</u>

SEQ ID NO: 44
AB3HU HUMANIZED LIGHT CHAIN VARIABLE LIGHT CHAIN AMINO ACID SEQUENCE.
COMPLEMENTARITY DETERMINING REGIONS ARE UNDERLINED
DIQMTQSPSSLSASVGDRVTITC<u>QSSPSVYSNYLS</u>WYQQKPGKVPKLLIY<u>YASTLAS</u>GVPSRFSGSGSGTDFTLTISSLQPE
DVATYYC<u>AGGYSSSTRAF</u>GGGTKVEIK

SEQ ID NO: 45
AB3HU HUMANIZED HEAVY CHAIN FULL-LENGTH NUCLEOTIDE SEQUENCE
CAGGAGCAGGTGAAGGAGACCGGGGGAGGCTTGGTACAGCCTGGGGGTCCCTGAGACTCTCCTGTGCAGCCTC
TGGATTCACCATCAGCAGCTATGGAGTGAGCTGGGTCCGCCAGGCTCCAGGGAAGGGGCTGGAGTGGGTCGCAT
TGATTTTTCCCGGGATTGGTTTCAAAGACTACGCGAGCTGGGTGAATGGCCGGTTCACCCTCTCAGCGACAACGC
CCAGAACACTGTGGAACTGCAAATGAACAGCCTGAGAGCCGAGGACACGGCCGTATATTACTGTGCGAGAGATTT
GGACTTGTGGGGCCAGGGAACCCTGGTCACCGTCTCGAGCGCTAGCACCAAGGGCCCATCGGTCTTCCCCCTGGC
ACCCTCCTCCAAGAGCACCTCTGGGGGCACAGCGGCCCTGGGCTGCCTGGTCAAGGACTACTTCCCCGAACCGGT
GACGGTGTCGTGGAACTCAGGCGCCCTGACCAGCGGCGTGCACACCTTCCCGGCTGTCCTACAGTCCTCAGGACT
CTACTCCCTCAGCAGCGTGGTGACCGTGCCCTCCAGCAGCTTGGGCACCCAGACCTACATCTGCAACGTGAATCAC
AAGCCCAGCAACACCAAGGTGGACAAGAGAGTTGAGCCCAAATCTTGTGACAAAACTCACACATGCCCACCGTGC
CCAGCACCTGAACTCCTGGGGGGACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCCAGCGACATCGCCGTG
GAGTGGGAGAGCAATGGGCAGCCGGAGAACAACTACAAGACCACGCCTCCCGTGCTGGACTCCGACGGCTCCTT
CTTCCTCTATAGCAAGCTCACCGTGGACAAGAGCAGGTGGCAGCAGGGGAACGTCTTCTCATGCTCCGTGATGCA
TGAGGCTCTGCACAACCACTACACGCAGAAGAGCCTCTCCCTGTCTCCGGGTAAA

SEQ ID NO: 46
AB3HU HUMANIZED HEAVY CHAIN VARIABLE HEAVY CHAIN NUCLEOTIDE SEQUENCE
CAGGAGCAGGTGAAGGAGACCGGGGGAGGCTTGGTACAGCCTGGGGGTCCCTGAGACTCTCCTGTGCAGCCTC
TGGATTCACCATCAGCAGCTATGGAGTGAGCTGGGTCCGCCAGGCTCCAGGGAAGGGGCTGGAGTGGGTCGCAT
TGATTTTTCCCGGGATTGGTTTCAAAGACTACGCGAGCTGGGTGAATGGCCGGTTCACCCTCTCAGCGACAACGC
CCAGAACACTGTGGAACTGCAAATGAACAGCCTGAGAGCCGAGGACACGGCCGTATATTACTGTGCGAGAGATTT
GGACTTGTGGGGCCAGGGAACCCTGGTCACCGTCTCGAGC

SEQ ID NO: 47
AB3HU HUMANIZED HEAVY CHAIN FULL-LENGTH AMINO ACID SEQUENCE. HUMAN GAMMA1
CONSTANT DOMAIN IS UNDERLINED
QEQVKETGGGLVQPGGSLRLSCAASGFTISSYGVSWVRQAPGKGLEWVALIFPGIGFKDYASWVNGRFTLSSDNAQN
TVELQMNSLRAEDTAVYYCARDLDLWGQGTLVTVSS<u>ASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSCDKTHTCPPCPAPELLGGPSV
FLFPPKPKDTLMISRTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK</u>

SEQ ID NO: 48
AB3HU HUMANIZED HEAVY CHAIN VARIABLE HEAVY CHAIN AMINO ACID SEQUENCE.
COMPLEMENTARITY DETERMINING REGIONS ARE UNDERLINED
QEQVKETGGGLVQPGGSLRLSCAASGFTIS<u>SYGVS</u>WVRQAPGKGLEWVA<u>LIFPGIGFKDYASWVNG</u>RFTLSSDNAQN
TVELQMNSLRAEDTAVYYCAR<u>DLDL</u>WGQGTLVTVSS

SEQUENCE LISTING

SEQ ID NO: 49
AB4 CHIMERIC LIGHT CHAIN FULL-LENGTH NUCLEOTIDE SEQUENCE
GCCCTTGTGATGACCCAGACTCCATCCTCCGTGTCTGCAGCTGTGGGAGGCACAGTCACCATCAATTGCCAGGCCA
GTCAGAACATTTACAGCAATTTAGCCTGGTATCAGCAGAAACCAGGGCAGCCTCCCAGCCTCCTGATCTACCAGGC
ATCCACTCTGGCATCTGGGGTCTCATCGCGGTTCAGCGGCAGTGGATATGGGACAGAGTTCACTCTCACCATCAGC
GACCTGGAGTGTGCCGATGCTGCCACTTACTACTGTCAAGGCGGTTATTATAGTGCTGCCCTTAATACTTTCGGCG
GAGGGACCGAGGTGGTGGTCAAACGTACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAGG
GCCTGAGCTCGCCCGTCACAAAGAGCTTCAACAGGGGAGAGTGT

SEQ ID NO: 50
AB4 CHIMERIC LIGHT CHAIN VARIABLE LIGHT CHAIN NUCLEOTIDE SEQUENCE
GCCCTTGTGATGACCCAGACTCCATCCTCCGTGTCTGCAGCTGTGGGAGGCACAGTCACCATCAATTGCCAGGCCA
GTCAGAACATTTACAGCAATTTAGCCTGGTATCAGCAGAAACCAGGGCAGCCTCCCAGCCTCCTGATCTACCAGGC
ATCCACTCTGGCATCTGGGGTCTCATCGCGGTTCAGCGGCAGTGGATATGGGACAGAGTTCACTCTCACCATCAGC
GACCTGGAGTGTGCCGATGCTGCCACTTACTACTGTCAAGGCGGTTATTATAGTGCTGCCCTTAATACTTTCGGCG
GAGGGACCGAGGTGGTGGTCAAA

SEQ ID NO: 51
AB4 CHIMERIC LIGHT CHAIN FULL-LENGTH AMINO ACID SEQUENCE. HUMAN KAPPA CONSTANT
DOMAIN IS UNDERLINED
ALVMTQTPSSVSAAVGGTVTINCQASQNIYSNLAWYQQKPGQPPSLLIYQASTLASGVSSRFSGSGYGTEFTLTISDLEC
ADAATYYCQGGYYSAALNTFGGGTEVVVK<u>RTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC</u>

SEQ ID NO: 52
AB4 CHIMERIC LIGHT CHAIN VARIABLE LIGHT CHAIN AMINO ACID SEQUENCE. COMPIMENTARITY
DETERMINING REGIONS ARE UNDERLINED
ALVMTQTPSSVSAAVGGTVTINC<u>QASQNIYSNLA</u>WYQQKPGQPPSLLIY<u>QASTLAS</u>GVSSRFSGSGYGTEFTLTISDLEC
ADAATYYC<u>QGGYYSAALNT</u>FGGGTEVVVK

SEQ ID NO: 53
AB4 CHIMERIC HEAVY CHAIN FULL-LENGTH NUCLEOTIDE SEQUENCE
CAGTCGCTGGAGGAGTCCGGGGGTCGCCTGGTCACGCCTGGGACACCCCTGACACTCACCTGCACAGTCTCTGGA
TTCTCCCTCAGTAGCTATGCAATGAGCTGGGTCCGCCAGGCTCCAGGGAAGGGGCTGGAATACATCGGATACATT
GGTGATACTACTGGCATAGCCTACGCGAGCTGGGCGAATGGCCGATTCACCATCTCCAAAACCTCGACCACGGTG
GATCTGAAGATCACCAGTCCGACAACCGGGGACACGGCCACCTATTTCTGTGCCAGAGGCTGGTCCTACTTAGAC
ATCTGGGGCCAAGGGACCCTGGTCACCGTCTCGAGCGCTGACACCAAGGGCCCATCGGTCTTCCCCCTGGCACCCT
CCTCCAAGAGCACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCAGGACTCTACTC
CCTCAGCAGCGTGGTGACCGTGCCCTCCAGCAGCTTGGGCACCCAGACCTACATCTGCAACGTGAATCACAAGCCC
AGCAACACCAAGGTGGACAAGAGAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACCCTCATGATCTCCCGGACCCC
TGAGGTCACATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGCAGCCCCGAGAACCACAGGTGTACACCCTGCCCCCATCCCGGGAG
GAGATGACCAAGAACCAGGTCAGCCTGACCTGCCTGGTCAAAGGCTTCTATCCCAGCGACATCGCCGTGGAGTGG
GAGAGCAATGGGCAGCCGGAGAACAACTACAAGACCACGCCTCCCGTGCTGGACTCCGACGGCTCCTTCTTCCTC
TATAGCAAGCTCACCGTGGACAAGAGCAGGTGGCAGCAGGGGAACGTCTTCTCATGCTCCGTGATGCATGAGGCT
CTGCACAACCACTACACGCAGAAGAGCCTCTCCCTGTCTCCGGGTAAA

SEQ ID NO: 54
AB4 CHIMERIC HEAVY CHAIN VARIABLE HEAVY CHAIN NUCLEOTIDE SEQUENCE
CAGTCGCTGGAGGAGTCCGGGGGTCGCCTGGTCACGCCTGGGACACCCCTGACACTCACCTGCACAGTCTCTGGA
TTCTCCCTCAGTAGCTATGCAATGAGCTGGGTCCGCCAGGCTCCAGGGAAGGGGCTGGAATACATCGGATACATT
GGTGATACTACTGGCATAGCCTACGCGAGCTGGGCGAATGGCCGATTCACCATCTCCAAAACCTCGACCACGGTG
GATCTGAAGATCACCAGTCCGACAACCGGGGACACGGCCACCTATTTCTGTGCCAGAGGCTGGTCCTACTTAGAC
ATCTGGGGCCAAGGGACCCTGGTCACCGTCTCGAGC

SEQ ID NO: 55
AB4 CHIMERIC HEAVY CHAIN FULL-LENGTH AMINO ACID SEQUENCE. HUMAN GAMMA-1 CONSTANT
DOMAIN IS UNDERLINED
QSLEESGGRLVTPGTPLTLTCTVSGFSLSSYAMSWVRQAPGKGLEYIGYIGDTTGIAYASWANGRFTISKTSTTVDLKITS
PTTGDTATYFCARGWSYLDIWGQGTLVTVSS<u>ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKRVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK</u>

SEQUENCE LISTING

SEQ ID NO: 56
AB4 CHIMERIC HEAVY CHAIN VARIABLE HEAVY CHAIN AMINO ACID SEQUENCE. COMPLIMENTARITY
DETERMINING REGIONS ARE UNDERLINED
QSLEESGGRLVTPGTPLTLTCTVSGFSLS<u>SYAMS</u>WVRQAPGKGLEYIG<u>YIGDTTGIAYASWANG</u>RFTISKTSTTVDLKITS
PTTGDTATYFCAR<u>GWSYLDI</u>WGQGTLVTVSS

SEQ ID NO: 57
AB4HU HUMANIZED LIGHT CHAIN FULL-LENGTH NUCLEOTIDE SEQUENCE
GCCCTTGTGATGACCCAGTCTCCATCCTCCCTGTCTGCATCTGTAGGAGACAGAGTCACCATCACTTGCCAGGCCA
GTCAGAACATTTACAGCAATTTAGCCTGGTATCAGCAGAAACCAGGGAAAGTTCCTAAGCTCCTGATCTATCAGGC
CTCCACTCTGGCATCTGGGGTCCCATCTCGGTTCAGTGGCAGTGGATATGGGACAGATTTCACTCTCACCATCAGC
AGCCTGCAGCCTGAAGATGTTGCAACTTATTACTGTCAAGGCGGTTATTATAGTGCTGCCCTTAATACTTTCGGCG
GAGGGACCAAGGTGGAGATCAAACGTACGGTGGCTGCACCATCTGTCTTCATCTTCCCGCCATCTGATGAGCAGTT
GAAATCTGGAACTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGCACCTACAGCC
TCAGCAGCACCCTGACGCTGAGCAAAGCAGACTACGAGAAACACAAAGTCTACGCCTGCGAAGTCACCCATCAGG
GCCTGAGCTCGCCCGTCACAAAGAGCTTCAACAGGGGAGAGTGT

SEQ ID NO: 58
AB4HU HUMANIZED LIGHT CHAIN VARIABLE LIGHT CHAIN NUCLEOTIDE SEQUENCE
GCCCTTGTGATGACCCAGTCTCCATCCTCCCTGTCTGCATCTGTAGGAGACAGAGTCACCATCACTTGCCAGGCCA
GTCAGAACATTTACAGCAATTTAGCCTGGTATCAGCAGAAACCAGGGAAAGTTCCTAAGCTCCTGATCTATCAGGC
CTCCACTCTGGCATCTGGGGTCCCATCTCGGTTCAGTGGCAGTGGATATGGGACAGATTTCACTCTCACCATCAGC
AGCCTGCAGCCTGAAGATGTTGCAACTTATTACTGTCAAGGCGGTTATTATAGTGCTGCCCTTAATACTTTCGGCG
GAGGGACCAAGGTGGAGATCAAA

SEQ ID NO: 59
AB4HU HUMANIZED LIGHT CHAIN FULL-LENGTH AMINO ACID SEQUENCE. HUMAN KAPPA CONSTANT
DOMAIN IS UNDERLINED
ALVMTQSPSSLSASVGDRVTITCQASQNIYSNLAWYQQKPGKVPKLLIYQASTLASGVPSRFSGSGYGTDFTLTISSLQPE
DVATYYCQGGYYSAALNTFGGGTKVEIK<u>RTVAAPSVFIFPPSDEQLKSGTASVVCLLNNFYPREAKVQWKVDNALQSG</u>
<u>NSQESVTEQDSKDSTYSLSSTLTLSKADYEKHKVYACEVTHQGLSSPVTKSFNRGEC</u>

SEQ ID NO: 60
AB4HU HUMANIZED LIGHT CHAIN VARIABLE LIGHT CHAIN AMINO ACID SEQUENCE.
COMPLEMENTARITY DETERMINING REGIONS ARE UNDERLINED
ALVMTQSPSSLSASVGDRVTITC<u>QASQNIYSNLA</u>WYQQKPGKVPKLLIY<u>QASTLAS</u>GVPSRFSGSGYGTDFTLTISSLQPE
DVATYYC<u>QGGYYSAALNT</u>FGGGTKVEIK

SEQ ID NO: 61
AB4HU HUMANIZED HEAVY CHAIN FULL-LENGTH NUCLEOTIDE SEQUENCE
GAGGTGCAGCTGGTGGAGTCTGGGGGAGGCTTGGTCCAGCCTGGGGGGTCCCTGAGACTCTCCTGTACAGCCTC
TGGATTCTCCCTCAGTAGCTATGCAATGAGCTGGGTCCGCCAGGCTCCAGGGAAGGGGCTGGAGTACATCGGCTA
CATTGGTGATACTACTGGCATAGCCTACGCGAGCTGGGCAATGGCAGATTCACCATCTCCAAAGACAATACCAA
GAACACGGTGGATCTTCAAATGAACAGCCTGAGAGCCGAGGACACGGCTGTGTATTACTGTGCGAGAGGCTGGT
CCTACTTAGACATCTGGGGCCAAGGGACCCTGGTCACCGTCTCGAGCGCTAGCACCAAGGGCCCATCGGTCTTCCC
CCTGGCACCCTCCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTCCTACAGTCCTC
AGGACTCTACTCCCTCAGCAGCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGACAAAACTCACACATGCCCA
CCGTGCCCAGCACCTGAAGCCGCGGGGGCACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACGTACCGTGT
GGTCAGCGTCCTCACCGTCCTGCACCAGGACTGGCTGAATGGCAAGGAGTACAAGTGCGCGGTCTCCAACAAAGC
CCTCCCAGCCCCCATCGAGAAAACCATCTCCAAAGCCAAAGGGCAGCCCCGAGAACCACAGGTGTACACCCTGCC
CCCATCCCGGGATGAGCTGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGACGG
CTCCTTCTTCCTCTATAGCAAGCTCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCTCCGGGT

SEQ ID NO: 62
AB4HU HUMANIZED HEAVY CHAIN VARIABLE HEAVY CHAIN NUCLEOTIDE SEQUENCE
GAGGTGCAGCTGGTGGAGTCTGGGGGAGGCTTGGTCCAGCCTGGGGGGTCCCTGAGACTCTCCTGTACAGCCTC
TGGATTCTCCCTCAGTAGCTATGCAATGAGCTGGGTCCGCCAGGCTCCAGGGAAGGGGCTGGAGTACATCGGCTA
CATTGGTGATACTACTGGCATAGCCTACGCGAGCTGGGCAATGGCAGATTCACCATCTCCAAAGACAATACCAA
GAACACGGTGGATCTTCAAATGAACAGCCTGAGAGCCGAGGACACGGCTGTGTATTACTGTGCGAGAGGCTGGT
CCTACTTAGACATCTGGGGCCAAGGGACCCTGGTCACCGTCTCGAGC

SEQ ID NO: 63
AB4HU HUMANIZED HEAVY CHAIN FULL-LENGTH AMINO ACID SEQUENCE. HUMAN GAMMA1
CONSTANT DOMAIN IS UNDERLINED
EVQLVESGGGLVQPGGSLRLSCTASGFSLSSYAMSWVRQAPGKGLEYIGYIGDUGIAYASWANGRFTISKDNTKNTVD
LQMNSLRAEDTAVYYCARGWSYLDIWGQGTLVTVSS<u>ASTKGPSVFPLAPSSKSTSGGTAALGCLVKDYFPEPVTVSWN</u>
<u>SGALTSGVHTFPAVLQSSGLYSLSSVVTVPSSSLGTQTYICNVNHKPSNTKVDKRVEPKSCDKTHTCPPCPAPEAAGAPS</u>
<u>VFLFPPKPKDTLMISRTPEVTCVVVDVSHEDPEVKFNWYVDGVEVHNAKTKPREEQYNSTYRVVSVLTVLHQDWLNG</u>
<u>KEYKCAVSNKALPAPIEKTISKAKGQPREPQVYTLPPSRDELTKNQVSLTCLVKGFYPSDIAVEWESNGQPENNYKTTPP</u>
<u>VLDSDGSFFLYSKLTVDKSRWQQGNVFSCSVMHEALHNHYTQKSLSLSPG</u>

SEQUENCE LISTING

SEQ ID NO: 64
AB4HU HUMANIZED HEAVY CHAIN VARIABLE HEAVY CHAIN AMINO ACID SEQUENCE.
COMPLEMENTARITY DETERMINING REGIONS ARE UNDERLINED
EVQLVESGGGLVQPGGSLRLSCTASGFSLS<u>SYAMS</u>WVRQAPGKGLEYIG<u>YIGDTTGIAYASWANG</u>RFTISKDNTKNTVD
LQMNSLRAEDTAVYYCAR<u>GWSYLDI</u>WGQGTLVTVSS

SEQ ID NO: 65
AB5 CHIMERIC LIGHT CHAIN FULL-LENGTH NUCLEOTIDE SEQUENCE
GCCTATGATATGACCCAGACTCCATCCTCCGTGTCTGCCGCTGTGGGAGGCACAGTCACCATCAATTGCCAGGCCA
GTCAGAGCATTAACAACCAACTATCCTGGTATCAGCAGAAACCAGGGCAGCCTCCCAAGCTCCTGATCTATGGTGC
ATCCACTCTGGCATCTGGGGTCCCATCGCGGTTCACCGGCAGTGGATCTGGGACAGAGTTCACTCTCACCATCAGC
GGCGTGCAGTGTGACGATGCTGCCACTTACTACTGTCATGTTCATTATTGCAGTGGTGGTAGTTGTTTTTGGGCTTT
CGGCGGAGGGACCGAGGTGGTGGTCAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGCAAGGACAGCACCTA
CAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGT

SEQ ID NO: 66
AB5 CHIMERIC LIGHT CHAIN VARIABLE LIGHT CHAIN NUCLEOTIDE SEQUENCE
GCCTATGATATGACCCAGACTCCATCCTCCGTGTCTGCCGCTGTGGGAGGCACAGTCACCATCAATTGCCAGGCCA
GTCAGAGCATTAACAACCAACTATCCTGGTATCAGCAGAAACCAGGGCAGCCTCCCAAGCTCCTGATCTATGGTGC
ATCCACTCTGGCATCTGGGGTCCCATCGCGGTTCACCGGCAGTGGATCTGGGACAGAGTTCACTCTCACCATCAGC
GGCGTGCAGTGTGACGATGCTGCCACTTACTACTGTCATGTTCATTATTGCAGTGGTGGTAGTTGTTTTTGGGCTTT
CGGCGGAGGGACCGAGGTGGTGGTCAAA

SEQ ID NO: 67
AB5 CHIMERIC LIGHT CHAIN FULL-LENGTH AMINO ACID SEQUENCE. HUMAN KAPPA CONSTANT
DOMAIN IS UNDERLINED
AYDMTQTPSSVSAAVGGTVTINCQASQSINNQLSWYQQKPGQPPKLLIYGASTLASGVPSRFTGSGSGTEFTLTISGVQ
CDDAATYYCHVHYCSGGSCFWAFGGGTEVVVK<u>RTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRGEC</u>

SEQ ID NO: 68
AB5 CHIMERIC LIGHT CHAIN VARIABLE LIGHT CHAIN AMINO ACID SEQUENCE. COMPIMENTARITY
DETERMINING REGIONS ARE UNDERLINED
AYDMTQTPSSVSAAVGGTVTINC<u>QASQSINNQL</u>SWYQQKPGQPPKLLIY<u>GASTLAS</u>GVPSRFTGSGSGTEFTLTISGVQ
CDDAATYY<u>CHVHYCSGGSCFWA</u>FGGGTEVVVK

SEQ ID NO: 69
AB5 CHIMERIC HEAVY CHAIN FULL-LENGTH NUCLEOTIDE SEQUENCE
CAGGAGCAGTTGGAGGAGTCCGGGGGAGACCTGGTCAAGCCTGAGGGATCCCTGACACTCACCTGCACAGCCTC
TGGATTCTCCTTCAGTAGCAGCCACTGGATATGCTGGGTCCGCCAGGCTCCAGGGAAGGGGCTGGAGTGGATCGC
ATGCATTTATACTGGTAGTATTGATGTCTTTTACTGTGCGAGCTGGGCGAAAGGCCGATTCACCATCTCCAAACCCT
CGTCGACCACGGTGACTCTGCAAGTGCCCAGTCTGACAGCCGCGGACACGGCCACCTATTTCTGTGCGAGAGCCG
CTAATACTGATACTACCTACTTTAACTTGTGGGGCCCAGGGACCCTCGTCACCGTCTCGAGCGCTAGCACCAAGGG
CCCATCGGTCTTCCCCCTGGCACCCTCCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGACCAGCGGCGTGCACACCTTCCCGGCT
GTCCTACAGTCCTCAGGACTCTACTCCCTCAGCAGCGTGGTGACCGTGCCCTCCAGCAGCTTGGGCACCCAGACCT
ACATCTGCAACGTGAATCACAAGCCCAGCAACACCAAGGTGGACAAGAGAGTTGAGCCCAAATCTTGTGACAAAA
CTCACACATGCCCACCGTGCCCAGCACCTGAACTCCTGGGGGGACCGTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAGGT
CAAGTTCAACTGGTACGTGGACGGCGTGGAGGTGCATAATGCCAAGACAAAGCCGCGGGAGGAGCAGTACAACA
GCACGTACCGTGTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTCAAAGGCTTCT
ATCCCAGCGACATCGCCGTGGAGTGGGAGAGCAATGGGCAGCCGGAGAACAACTACAAGACCACGCCTCCCGTG
CTGGACTCCGACGGCTCCTTCTTCCTCTATAGCAAGCTCACCGTGGACAAGAGCAGGTGGCAGCAGGGGAACGTC
TTCTCATGCTCCGTGATGCATGAGGCTCTGCACAACCACTACACGCAGAAGAGCCTCTCCCTGTCTCCGGGTAAA

SEQ ID NO: 70
AB5 CHIMERIC HEAVY CHAIN VARIABLE HEAVY CHAIN NUCLEOTIDE SEQUENCE
CAGGAGCAGTTGGAGGAGTCCGGGGGAGACCTGGTCAAGCCTGAGGGATCCCTGACACTCACCTGCACAGCCTC
TGGATTCTCCTTCAGTAGCAGCCACTGGATATGCTGGGTCCGCCAGGCTCCAGGGAAGGGGCTGGAGTGGATCGC
ATGCATTTATACTGGTAGTATTGATGTCTTTTACTGTGCGAGCTGGGCGAAAGGCCGATTCACCATCTCCAAACCCT
CGTCGACCACGGTGACTCTGCAAGTGCCCAGTCTGACAGCCGCGGACACGGCCACCTATTTCTGTGCGAGAGCCG
CTAATACTGATACTACCTACTTTAACTTGTGGGGCCCAGGGACCCTCGTCACCGTCTCGAGC

SEQUENCE LISTING

SEQ ID NO: 71
AB5 CHIMERIC HEAVY CHAIN FULL-LENGTH AMINO ACID SEQUENCE. HUMAN GAMMA-1 CONSTANT
DOMAIN IS UNDERLINED
QEQLEESGGDLVKPEGSLTLTCTASGFSFSSSHWICWVRQAPGKGLEWIACIYTGSIDVFYCASWAKGRFTISKPSSTTVT
LQVPSLTAADTATYFCARAANTDTTYFNLWGPGTLVTVSS<u>ASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK</u>

SEQ ID NO: 72
AB5 CHIMERIC HEAVY CHAIN VARIABLE HEAVY CHAIN AMINO ACID SEQUENCE. COMPLIMENTARITY
DETERMINING REGIONS ARE UNDERLINED
QEQLEESGGDLVKPEGSLTLTCTASGFSFSS<u>SHWIC</u>WVRQAPGKGLEWIA<u>CIYTGSIDVFYCASWAKG</u>RFTISKPSSTTVT
LQVPSLTAADTATYFCAR<u>AANTDTTYFNL</u>WGPGTLVTVSS

SEQ ID NO: 73
AB5HU HUMANIZED LIGHT CHAIN FULL-LENGTH NUCLEOTIDE SEQUENCE
GCCTATGATATGACCCAGTCTCCATCCTCCCTGTCTGCATCTGTAGGAGACAGAGTCACCATCAATTGCCAGGCCA
GTCAGAGCATTAACAACCAACTATCCTGGTATCAGCAGAAACCAGGGAAAGTTCCTAAGCTCCTGATCTATGGTGC
ATCCACTCTGGCATCTGGGGTCCCATCTCGGTTCACCGGCAGTGGATCTGGGACAGATTTCACTCTCACCATCAGC
AGCCTGCAGCCTGAAGATGTTGCAACTTATTACTGTCATGTTCATTATTGCAGTGGTGGTAGTTGTTTTTGGGCTTT
CGGCGGAGGGACCAAGGTGGAGATCAAACGTACGGTGGCTGCACCATCTGTCTTCATCTTCCCGCCATCTGATGA
GCAGTTGAAATCTGGAACTGCCTCTGTTGTGTGCCTGCTGAATAACTTCTATCCCAGAGAGGCCAAAGTACAGTGG
AAGGTGGATAACGCCCTCCAATCGGGTAACTCCCAGGAGAGTGTCACAGAGCAGGACAGCAAGGACAGCACCTA
CAGCCTCAGCAGCACCCTGACGCTGAGCAAAGCAGACTACGAGAAACACAAAGTCTACGCCTGCGAAGTCACCCA
TCAGGGCCTGAGCTCGCCCGTCACAAAGAGCTTCAACAGGGGAGAGTGT

SEQ ID NO: 74
AB5HU HUMANIZED LIGHT CHAIN VARIABLE LIGHT CHAIN NUCLEOTIDE SEQUENCE
GCCTATGATATGACCCAGTCTCCATCCTCCCTGTCTGCATCTGTAGGAGACAGAGTCACCATCAATTGCCAGGCCA
GTCAGAGCATTAACAACCAACTATCCTGGTATCAGCAGAAACCAGGGAAAGTTCCTAAGCTCCTGATCTATGGTGC
ATCCACTCTGGCATCTGGGGTCCCATCTCGGTTCACCGGCAGTGGATCTGGGACAGATTTCACTCTCACCATCAGC
AGCCTGCAGCCTGAAGATGTTGCAACTTATTACTGTCATGTTCATTATTGCAGTGGTGGTAGTTGTTTTTGGGCTTT
CGGCGGAGGGACCAAGGTGGAGATCAAA

SEQ ID NO: 75
AB5HU HUMANIZED LIGHT CHAIN FULL-LENGTH AMINO ACID SEQUENCE. HUMAN KAPPA CONSTANT
DOMAIN IS UNDERLINED
AYDMTQSPSSLSASVGDRVTINCQASQSINNQLSWYQQKPGKVPKLLIYGASTLASGVPSRFTGSGSGTDFTLTISSLQP
EDVATYYCHVHYCSGGSCFWAFGGGTKVEIK<u>RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC</u>

SEQ ID NO: 76
AB5HU HUMANIZED LIGHT CHAIN VARIABLE LIGHT CHAIN AMINO ACID SEQUENCE.
COMPLEMENTARITY DETERMINING REGIONS ARE UNDERLINED
AYDMTQSPSSLSASVGDRVTINC<u>QASQSINNQL</u>SWYQQKPGKVPKLLIY<u>GASTLAS</u>GVPSRFTGSGSGTDFTLTISSLQP
EDVATYYC<u>HVHYCSGGSCFWA</u>FGGGTKVEIK

SEQ ID NO: 77
AB5HU HUMANIZED HEAVY CHAIN FULL-LENGTH NUCLEOTIDE SEQUENCE
GAGGTGCAGCTGTTGGAGTCTGGGGGAGGCTTGGTACAGCCTGGGGGGTCCCTGAGACTCTCCTGTGCAGCCTCT
GGATTCACCTTTAGCAGCAGCCACTGGATATGCTGGGTCCGCCAGGCTCCAGGGAAGGGGCTGGAGTGGATCGC
ATGCATTTATACTGGTAGTATTGATGTCTTTTACTACGCGAGCTGGGCGAAAGGCCGGTTCACCATCTCCAGAGAC
AATTCCAAGAACACGCTGTATCTGCAAATGAACAGCCTGAGAGCCGAGGACACGGCCGTATATTACTGTGCGAGA
GCCGCTAATACTGATACTACCACTTTAACTTGTGGGGCCAGGGAACCCTGGTCACCGTCTCGAGCGCTAGCACCA
AGGGCCCATCGGTCTTCCCCCTGGCACCCTCCTCCAAGAGCACCTCTGGGGGCACAGCGGCCCTGGGCTGCCTGG
TCAAGGACTACTTCCCCGAACCGGTGACGGTGTCGTGGAACTCAGGCGCCCTGACCAGCGGCGTGCACACCTTCC
CGGCTGTCCTACAGTCCTCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAGAGTTGAGCCCAAATCTTGTGA
CAAAACTCACACATGCCCACCGTGCCCAGCACCTGAAGCCGCGGGGGCACCGTCAGTCTTCCTCTTCCCCCCAAAA
CCCAAGGACACCCTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCGGGAGGAGCAGT
ACAACAGCACGTACCGTGTGGTCAGCGTCCTCACCGTCCTGCACCAGGACTGGCTGAATGGCAAGGAGTACAAGT
GCGCGGTCTCCAACAAAGCCCTCCCAGCCCCCATCGAGAAAACCATCTCCAAAGCCAAAGGGCAGCCCCGAGAAC
CACAGGTGTACACCCTGCCCCCATCCCGGGATGAGCTGACCAAGAACCAGGTCAGCCTGACCTGCCTGGTCAAAG
GCTTCTATCCCAGCGACATCGCCGTGGAGTGGGAGAGCAATGGGCAGCCGGAGAACAACTACAAGACCACGCCT
CCCGTGCTGGACTCCGACGGCTCCTTCTTCCTCTATAGCAAGCTCACCGTGGACAAGAGCAGGTGGCAGCAGGGG
AACGTCTTCTCATGCTCCGTGATGCATGAGGCTCTGCACAACCACTACACGCAGAAGAGCCTCTCCCTGTCTCCGG
GT

SEQUENCE LISTING

SEQ ID NO: 78
AB5HU HUMANIZED HEAVY CHAIN VARIABLE HEAVY CHAIN NUCLEOTIDE SEQUENCE
GAGGTGCAGCTGTTGGAGTCTGGGGGAGGCTTGGTACAGCCTGGGGGGTCCCTGAGACTCTCCTGTGCAGCCTCT
GGATTCACCTTTAGCAGCAGCCACTGGATATGCTGGGTCCGCCAGGCTCCAGGGAAGGGGCTGGAGTGGATCGC
ATGCATTTATACTGGTAGTATTGATGTCTTTTACTACGCGAGCTGGGCGAAAGGCCGGTTCACCATCTCCAGAGAC
AATTCCAAGAACACGCTGTATCTGCAAATGAACAGCCTGAGAGCCGAGGACACGGCCGTATATTACTGTGCGAGA
GCCGCTAATACTGATACCTACTTTAACTTGTGGGGCCAGGGAACCCTGGTCACCGTCTCGAGC

SEQ ID NO: 79
AB5HU HUMANIZED HEAVY CHAIN FULL-LENGTH AMINO ACID SEQUENCE. HUMAN GAMMA1
CONSTANT DOMAIN IS UNDERLINED
EVQLLESGGGLVQPGGSLRLSCAASGFTFSSSHWICWVRQAPGKGLEWIACIYTGSIDVFYYASWAKGRFTISRDNSKN
TLYLQMNSLRAEDTAVYYCARAANTDTTYFNLWGQGTLVTVSS<u>ASTKGPSVFPLAPSSKSTSGGTAALGCLVKDYFPEP
VTVSWNSGALTSGVHTFPAVLQSSGLYSLSSVVTVPSSSLGTQTYICNVNHKPSNTKVDKRVEPKSCDKTHTCPPCPAPE
AAGAPSVFLFPPKPKDTLMISRTPEVTCVVVDVSHEDPEVKFNWYVDGVEVHNAKTKPREEQYNSTYRVVSVLTVLHQ
DWLNGKEYKCAVSNKALPAPIEKTISKAKGQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKSLSLSPG</u>

SEQ ID NO: 80
AB5HU HUMANIZED HEAVY CHAIN VARIABLE HEAVY CHAIN AMINO ACID SEQUENCE.
COMPLEMENTARITY DETERMINING REGIONS ARE UNDERLINED
EVQLLESGGGLVQPGGSLRLSCAASGFTFSS<u>SHWIC</u>WVRQAPGKGLEWIA<u>CIYTGSIDVFYYASWAKG</u>RFTISRDNSKN
TLYLQMNSLRAEDTAVYYCAR<u>AANTDTTYFNL</u>WGQGTLVTVSS

---

What is claimed is:

1. An isolated mAb having a binding specificity to human PD-1, comprising an amino acid sequence of SEQ ID NO:52, and an amino acid sequence of SEQ ID NO:56.

2. The isolated mAb according to claim 1, exhibiting one or more functional properties selected from high affinity binding to human PD-1, inhibiting binding of human PD-L1 to PD-1, enhancing T cell activation, stimulating antibody response, reversing the suppressive function of an immunosuppressive cell, or a combination thereof.

3. The isolated mAb according to claim 1, wherein the isolated mAb is a humanized antibody, a chimeric antibody, or a recombinant antibody.

4. The isolated mAb according to claim 1, wherein the isolated mAb comprises an IgG.

5. The isolated mAb according to claim 1, wherein the isolated mAb further comprises a Fv, a Fab, a F(ab')2, a scFV or a scFV2 fragment.

6. The isolated mAb according to claim 1, wherein the isolated mAb comprises a bispecific antibody, tri-specific antibody, or multi•specific antibody.

7. An isolated nucleic acid encoding the isolated mAb according to claim 1.

8. An expression vector comprising the isolated nucleic acid of claim 7.

9. A host cell comprising the nucleic acid of claim 7, wherein the host cell is a prokaryotic cell or a eukaryotic cell.

10. A method of producing an antibody comprising culturing the host cell of claim 9, so that the antibody is produced.

11. An immuno-conjugate, comprising the isolated mAb thereof according to claim 1 and a drug unit, wherein the drug unit is selected from a cytotoxic agent, an immune regulatory reagent, a combination thereof.

12. A pharmaceutical composition, comprising the isolated mAb or antigen-binding fragment thereof according to claim 1 and a pharmaceutically acceptable carrier.

13. The pharmaceutical composition of claim 12, further comprising a therapeutic agent.

14. A method of treating a subject with a cancer, comprising administering to the subject an effective amount of the isolated mAb according to claim 1, wherein the cancer comprises cells expressing PD-1.

15. The method of claim 14, further comprising co-administering an effective amount of a therapeutic agent, wherein the therapeutic agent comprises capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, or a derivative or a combination thereof.

16. The method of claim 14, wherein the subject is a human.

* * * * *